United States Patent
Haldar et al.

(10) Patent No.: US 9,636,356 B2
(45) Date of Patent: May 2, 2017

(54) NANOPARTICLE COMPOSITIONS OF ANTIBACTERIAL COMPOUNDS AND OTHER USES THEREOF

(71) Applicant: JAWAHARLAL NEHRU CENTRE FOR ADVANCED SCIENTIFIC RESEARCH, Bangalore, Karnataka (IN)

(72) Inventors: Jayanta Haldar, Bangalore (IN); Divakara Siva Sathyanarayana Murthy Uppu, Bangalore (IN); Padma Akkapeddi, Bangalore (IN); Goutham Belagula Manjunath, Bangalore (IN)

(73) Assignee: JAWAHARLAL NEHRU CENTRE FOR ADVANCED SCIENTIFIC RESEARCH, Bangalore (IN)

( * ) Notice: Subject to any disclaimer, the term of this patent is extended or adjusted under 35 U.S.C. 154(b) by 103 days.

(21) Appl. No.: 14/421,086

(22) PCT Filed: Jul. 5, 2013

(86) PCT No.: PCT/IB2013/055518
§ 371 (c)(1),
(2) Date: Feb. 11, 2015

(87) PCT Pub. No.: WO2014/006601
PCT Pub. Date: Jan. 9, 2014

(65) Prior Publication Data
US 2015/0238521 A1    Aug. 27, 2015

(30) Foreign Application Priority Data

Jul. 6, 2012 (IN) ............... 2747/CHE/2012

(51) Int. Cl.
*C08F 220/52* (2006.01)
*A61K 31/787* (2006.01)
(Continued)

(52) U.S. Cl.
CPC ............ *A61K 31/787* (2013.01); *A61K 9/14* (2013.01); *A61L 27/54* (2013.01); *A61L 29/16* (2013.01);
(Continued)

(58) Field of Classification Search
CPC ......... A61K 31/787; A61K 9/14; A61L 27/54; A61L 29/16; A61L 31/16;
(Continued)

(56) References Cited

U.S. PATENT DOCUMENTS 3,340,680 A * 9/1967 Fields ............... A61L 9/01
422/4
3,655,869 A * 4/1972 Wharton ............... A61K 31/785
424/78.01
4,544,621 A * 10/1985 Roth ............... C08F 20/36
430/271.1

FOREIGN PATENT DOCUMENTS

WO    2011095867 A1    8/2011
WO    WO2011/095867 A1 *  8/2011 ............ C08F 212/08

OTHER PUBLICATIONS

Volodymyr Boyko et al., "Characterization of Polyelectrolyte Complexes Based on Maleic Anhydride Alternating Copolymers by Static and Dynamic Light Scattering," Apr. 3, 2007; Macromolecular Chemistry and Physics, 208(7):710-717; XP055088469.*

(Continued)

*Primary Examiner* — Sue Liu
*Assistant Examiner* — Erin Hirt
(74) *Attorney, Agent, or Firm* — Oliff PLC

(57) ABSTRACT

The present disclosure relates to the development of antibacterial compounds and their nanoparticle compositions. Methods of making the compounds and their nanoparticle compositions, their use as medicament for the treatment of (Continued)

bacterial infection and also for suppressing potentially harmful inflammation are disclosed.

20 Claims, 11 Drawing Sheets

(51) Int. Cl.
    *C08F 210/10*     (2006.01)
    *A61K 9/14*     (2006.01)
    *C08F 222/40*     (2006.01)
    *C09D 123/22*     (2006.01)
    *C09D 135/00*     (2006.01)
    *C08L 23/22*     (2006.01)
    *C08L 35/00*     (2006.01)
    *A61L 27/54*     (2006.01)
    *A61L 29/16*     (2006.01)
    *A61L 31/16*     (2006.01)
    *C08F 8/02*     (2006.01)
    *C08F 8/12*     (2006.01)
    *C08F 8/30*     (2006.01)
    *C08F 8/32*     (2006.01)
    *C08F 8/44*     (2006.01)
    *C08F 8/48*     (2006.01)
    *B82Y 40/00*     (2011.01)
(52) U.S. Cl.
    CPC ............... *A61L 31/16* (2013.01); *C08F 8/02* (2013.01); *C08F 8/12* (2013.01); *C08F 8/30* (2013.01); *C08F 8/32* (2013.01); *C08F 8/44* (2013.01); *C08F 8/48* (2013.01); *C08F 210/10* (2013.01); *C08F 220/52* (2013.01); *C08F 222/40* (2013.01); *C08L 23/22* (2013.01); *C08L 35/00* (2013.01); *C09D 123/22* (2013.01); *C09D 135/00* (2013.01); *A61L 2300/404* (2013.01); *A61L 2300/624* (2013.01); *A61L 2400/12* (2013.01); *B82Y 40/00* (2013.01); *C08F 2800/10* (2013.01)

(58) Field of Classification Search
    CPC ......... A61L 2300/404; A61L 2300/624; A61L 2400/12; C08F 8/02; C08F 8/12; C08F 8/30; C08F 8/32; C08F 8/44; C08F 8/48; C08F 210/10; C08F 220/52; C08F 222/40; C08F 2800/10; C08L 23/22; C08L 35/00; C09D 123/22; C09D 135/00; B82Y 40/00
    See application file for complete search history.

(56) References Cited

OTHER PUBLICATIONS

Feb. 3, 2014 International Search Report issued in International Patent Application No. PCT/IB2013/055518.
Volodymyr Boyko et al.; "Characterization of Polyelectrolyte Complexes Based on Maleic Anhydride Alternating Copolymers by Static and Dynamic Light Scattering;" Macromolecular Chemistry and Physics; vol. 208, No. 7; Apr. 3, 2007; pp. 710-717; XP055088469.
Sep. 24, 2014 Written Opinion issued in International Patent Application No. PCT/IB2013/055518.
Feb. 3, 2014 Written Opinion issued in International Patent Application No. PCT/IB2013/055518.
Nov. 10, 2014 International Preliminary Report on Patentability issued in International Application No. PCT/IB2013/055518.

* cited by examiner

NANOPARTICLE COMPOSITIONS OF ANTIBACTERIAL COMPOUNDS AND OTHER USES THEREOF

FIELD OF DISCLOSURE

The present disclosure relates to the field of medicinal chemistry, particularly to the development of antibacterial compounds and their nanoparticle compositions. More, specifically it relates to the synthesis and characterization of cationic antibacterial compounds and compositions. The disclosed compounds and their compositions exhibit antibacterial activity against both Gram positive bacteria and Gram negative bacteria including drug resistant bacteria and suppress potentially harmful inflammation.

BACKGROUND

Bacterial infections are a major global health problem affecting millions of people worldwide. The ongoing explosion of resistant superbugs coupled with the diminishing antibiotic pipeline creates an urgent need for the development of new antimicrobial agents which exert novel mechanisms of action. Thus, there is an urgent need to develop new compounds and/or compositions that can have direct antibacterial activity even against drug-resistant bacteria.

The present invention relates to the development of antibacterial compounds and their nanoparticle compositions. More, specifically it relates to the synthesis and characterization of cationic antibacterial compounds and compositions. The disclosed compounds and their compositions exhibit antibacterial activity against both Gram positive bacteria and Gram negative bacteria including drug resistant bacteria and suppress potentially harmful inflammation.

SUMMARY OF INVENTION

In some embodiments the invention describes a compound of formula I:

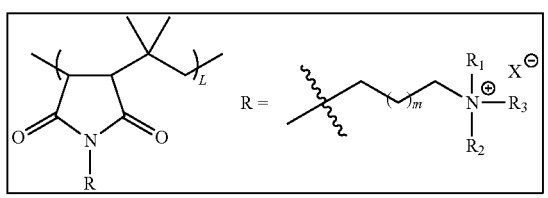

Formula I wherein, 'm' is an integer ranging from 0 to 1; 'L' is an integer ranging from 1 to 100; $R_1$, $R_2$ and $R_3$ are, independently at each occurrence, a hydrogen atom or methyl radical or $C_2$-$C_{40}$ aliphatic radical or $C_3$-$C_{40}$ aromatic radical or combinations thereof; and 'X' is selected from a group consisting of chloride, bromide, iodide, salicylate, 4-aminosalicylate, phosphomycin ((−)-(1R,2S)-(1,2-Epoxypropyl) phosphonate) and terephthalate.

In another embodiment the invention describes a compound of formula II:

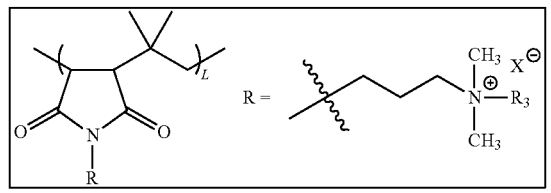

Formula II wherein, $R_3$ is a hydrogen atom or $C_1$-$C_{10}$ aliphatic radical, L is an integer 39 and X is a bromide.

Another embodiment of the invention provides the compound of Formula I, nanoparticle composition of compound of Formula I, a pharmaceutically acceptable salt, or any composition thereof for use as medicament. In some embodiments, the invention provides the compound of Formula I, a nanoparticle composition of compound of Formula I, a pharmaceutically acceptable salt or any composition thereof for use in treatment of a bacterial infection.

Still another embodiment of the invention provides the compound of Formula II, nanoparticle composition of compound of Formula II, a pharmaceutically acceptable salt, or any composition thereof for use as medicament. In some embodiments, the invention provides the compound of Formula II, a nanoparticle composition of compound of Formula II, a pharmaceutically acceptable salt or any composition thereof for use in treatment of a bacterial infection.

Yet another embodiment of the invention provides a method for treatment of a bacterium in a subject the method including steps of administering to the subject an effective amount of compound of Formula I or Formula II, a nanoparticle composition of compound of Formula I or Formula II, a pharmaceutically acceptable salt of Formula I or Formula II, or any composition thereof.

Still another embodiment of the invention provides a method of suppressing potentially harmful inflammation comprising administering to a subject suffering from sepsis the compound of Formula I or Formula II, a nanoparticle composition of compound of Formula I or Formula II, a pharmaceutically acceptable salt of Formula I or Formula II, or any composition thereof.

BRIEF DESCRIPTION OF ACCOMPANYING FIGURES

The features of the present disclosure will become more fully apparent from the following description taken in conjunction with the accompanying drawings. Understanding that the drawing depict only several embodiments in accordance with the disclosure and is therefore, not to be considered limiting of its scope, the disclosure will be described with additional specificity and detail through use of the accompanying drawing:

FIG. 1 provides general formula of the quaternized amphiphilic PIBMI derivatives.

Figure 5:
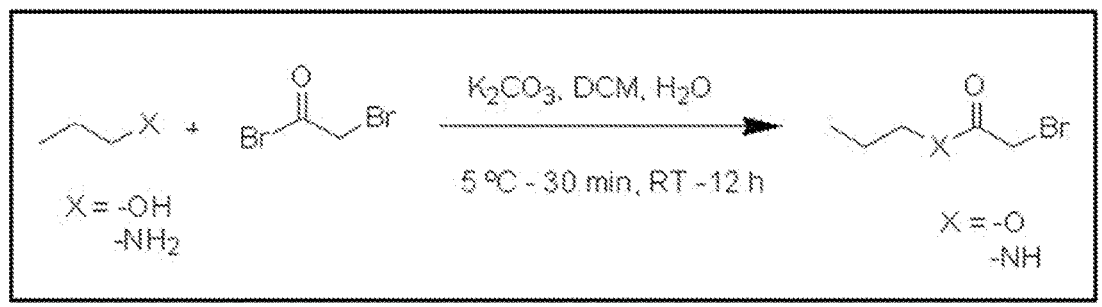
Figure 6:
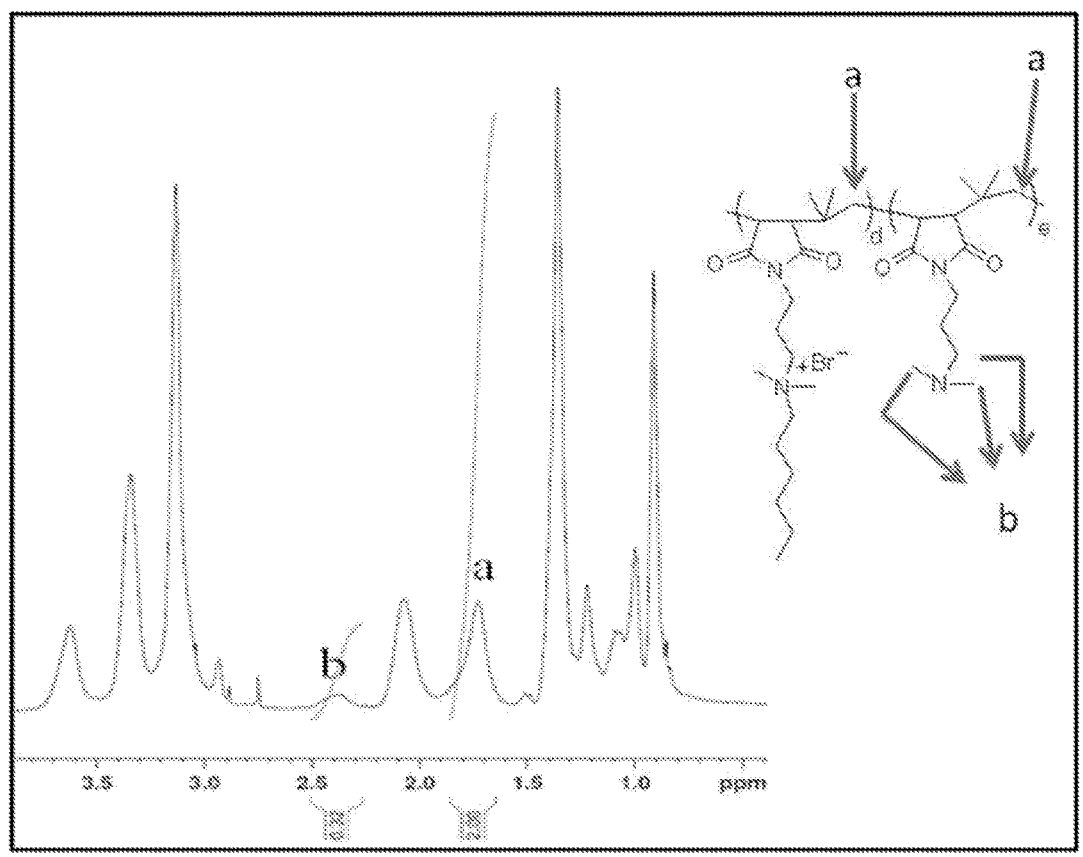

FIG. 5 provides general synthetic route for the synthesis of ester and amide based alkylating agents FIG. 6 relates to the $^1$H NMR of QHex_PIBMI (in D$_2$O) indicating the peaks used for the calculation of degree of quaternization (δ/ppm).

Figure 7:
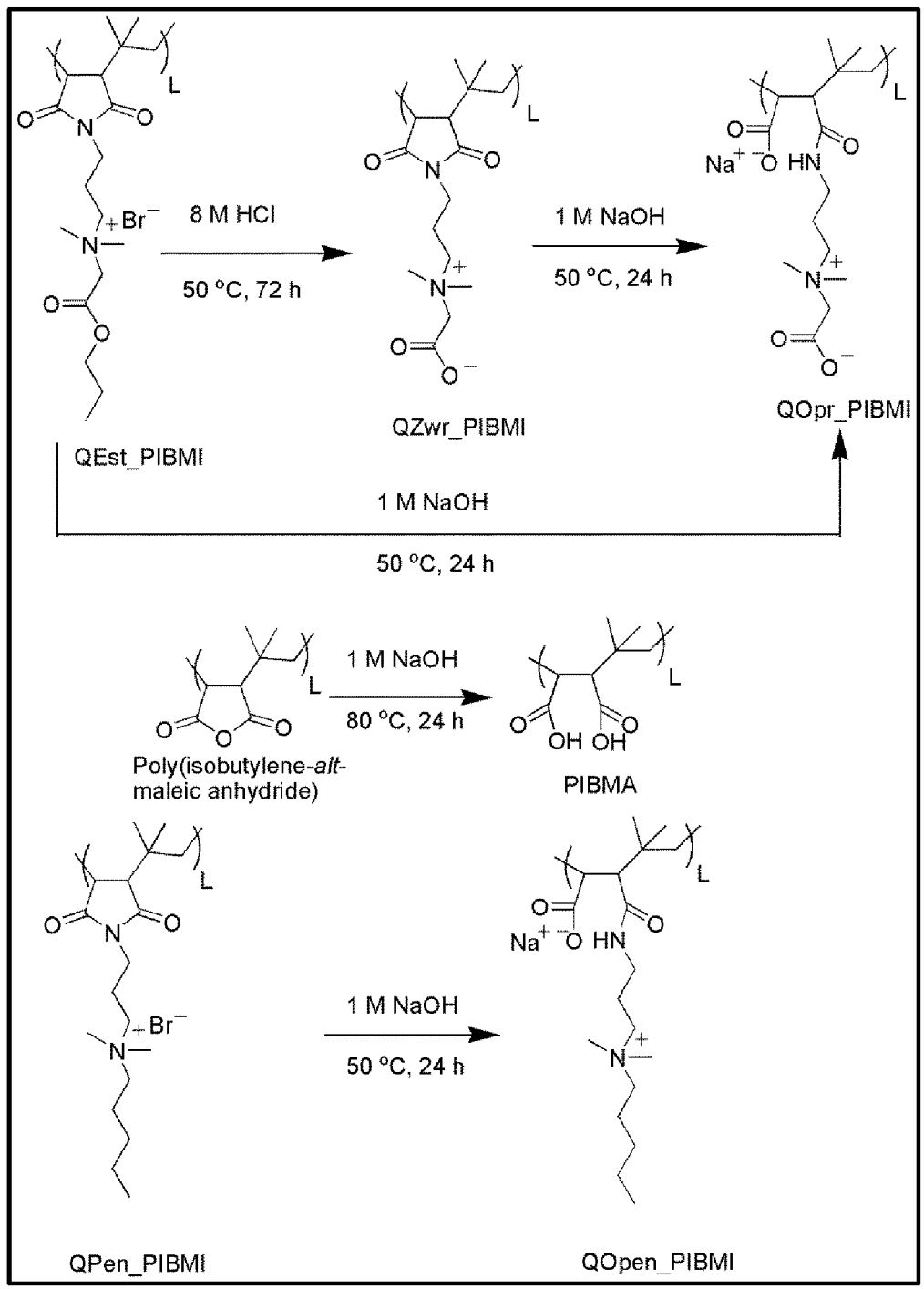

FIG. 7 shows the synthesis of degradation by-products of QEst_PIBMI, QPen_PIBMI and poly(isobutylene-alt-maleic anhydride).

Figure 8:
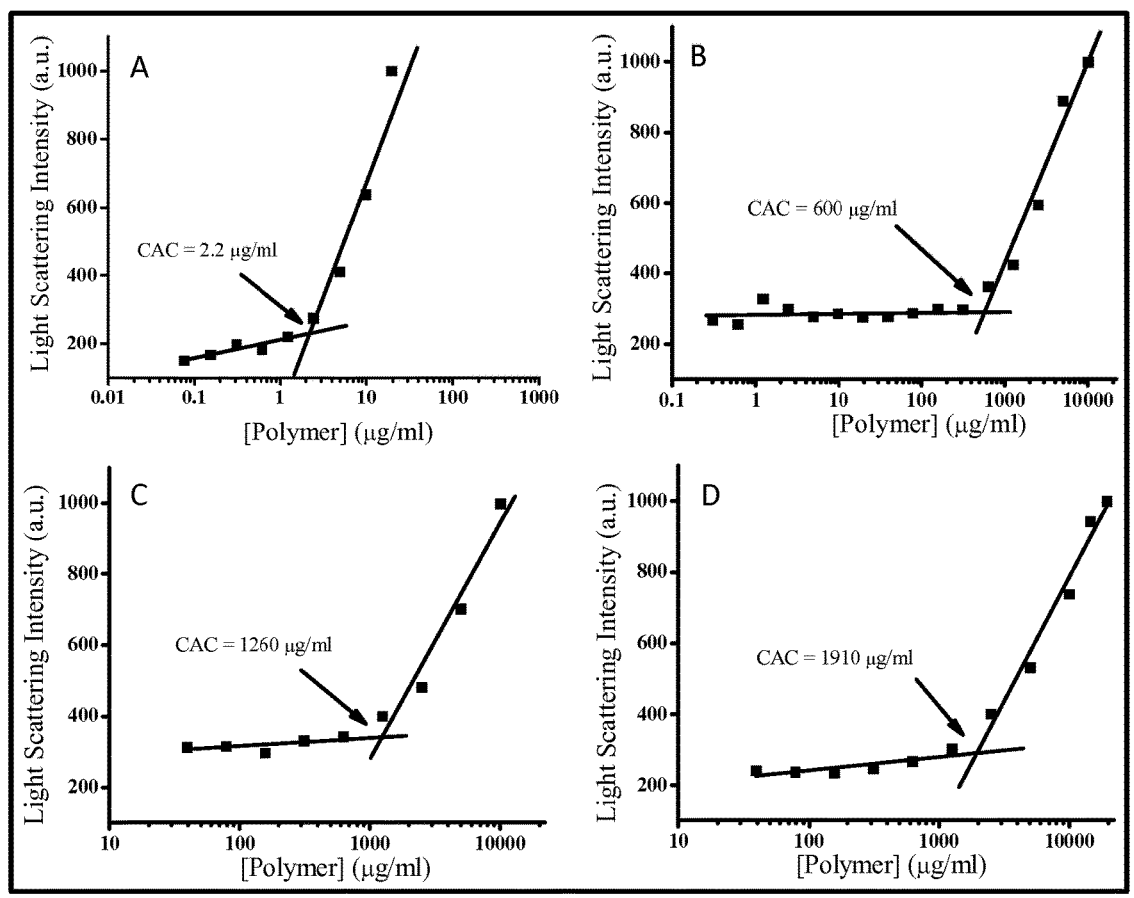

FIG. 8 provides graph showing aggregation properties of quaternized amphiphilic PIBMI derivatives—(A) QHex_PIBMI in MH broth, (B) QHex_PIBMI in PBS, (C) QAmi_PIBMI in PBS and (D) QEst_PIBMI in PBS respectively.

Figure 9:
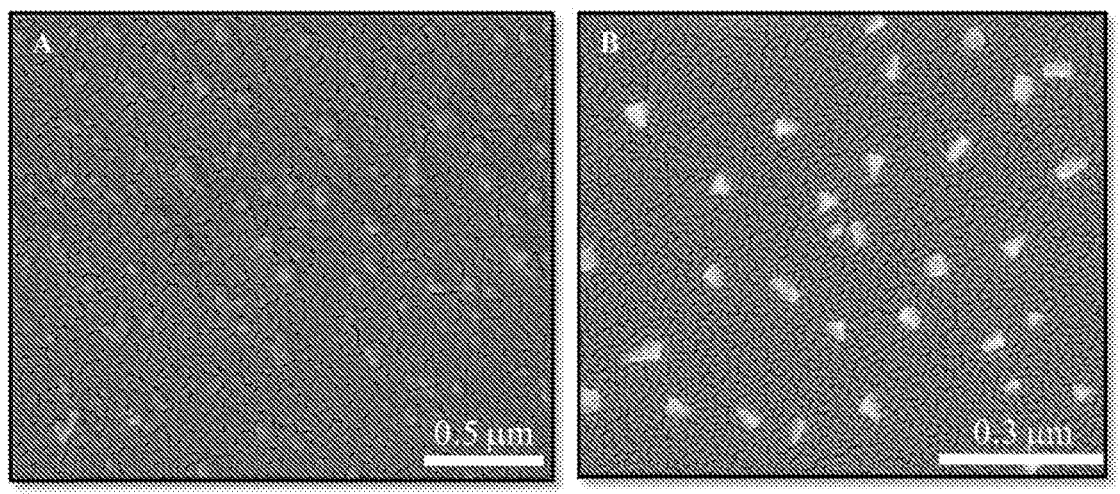

FIG. 9 provides scanning electron microscopy (SEM) images of the nanoparticles formed by the quaternized amphiphilic PIBMI derivatives in aqueous solution. (A) QHEx_PIBMI and (B) QEst_PIBMI.

Figure 10:
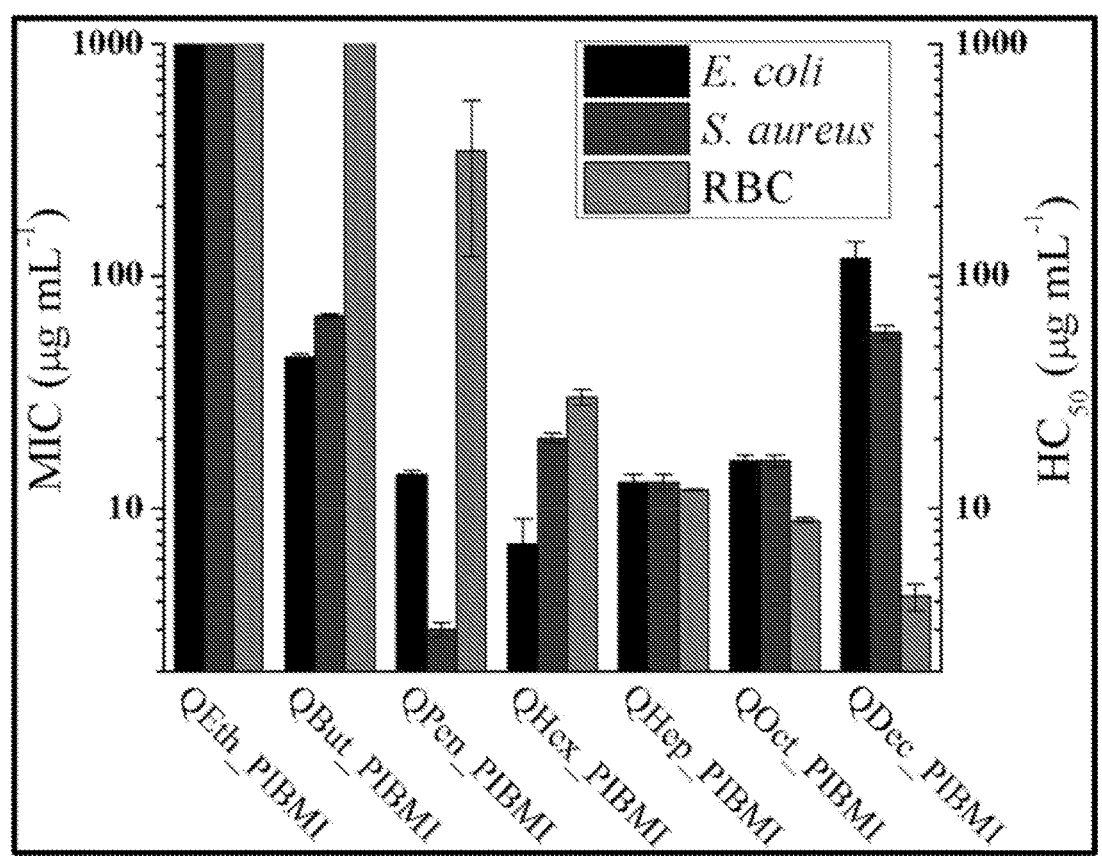

FIG. 10 shows the antibacterial and hemolytic activity of the quaternized PIBMI derivatives with different alkyl chain lengths ranging from ethyl to decyl (C2 to C10). The MIC data are the average of results from three independent experiments of each derivative performed in triplicate. Error bar: standard error of the mean.

Figure 11:
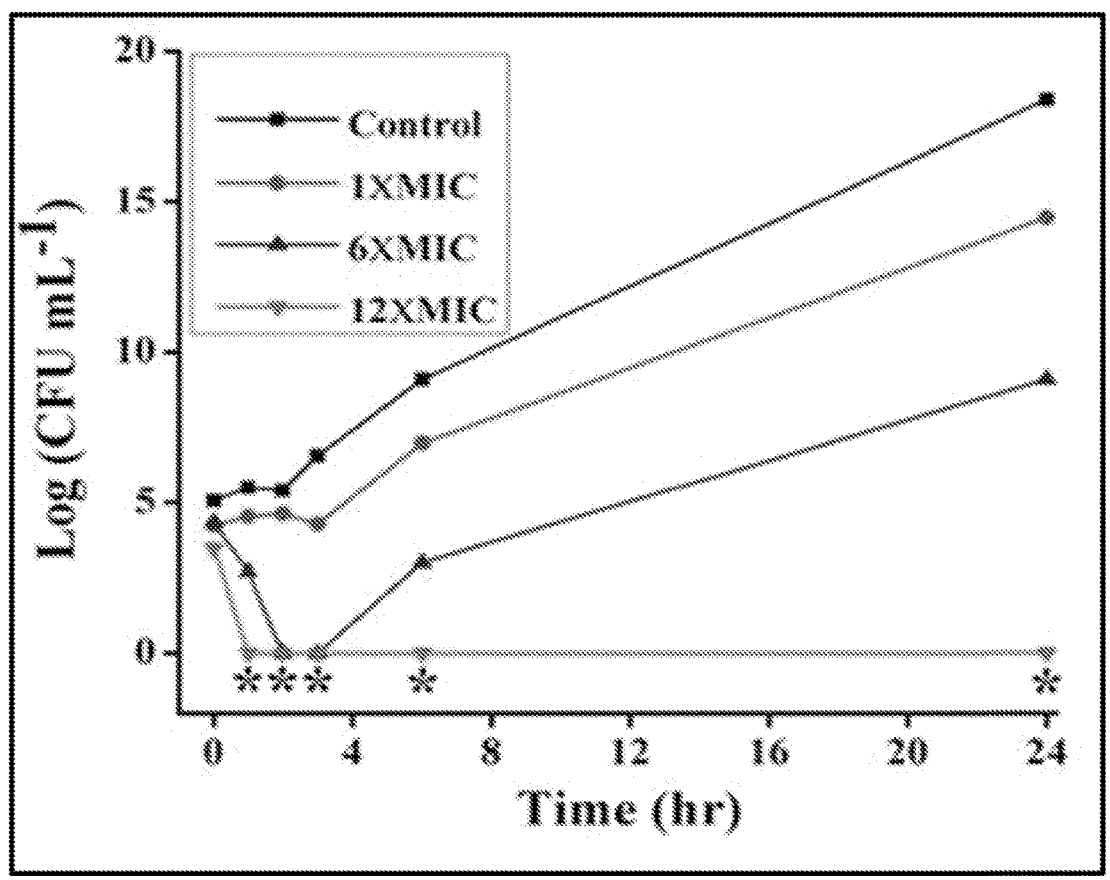

FIG. 11 relates to graphical representation of the bactericidal time-kill kinetics of QAmi_PIBMI against *S. aureus* (stars represent <50 CFU/mL)

Figure 12:
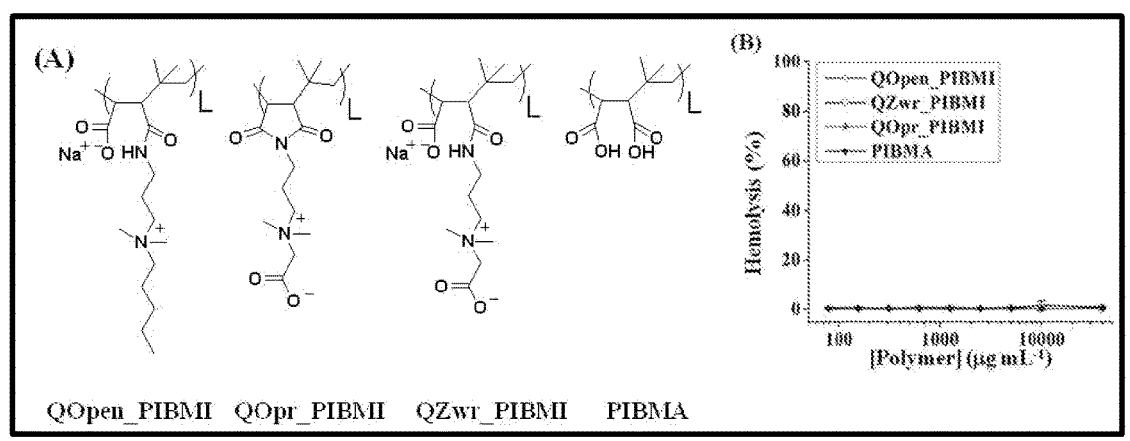

FIG. 12 shows (A) the degraded polymeric by-products of the quaternized derivatives QPen_PIBMI, QEst_PIBMI and poly(isobutylene-alt-maleic anhydride) and (B) hemolytic activities of their degradation products up to 40000 μg mL$^{-1}$.

Figure 13:
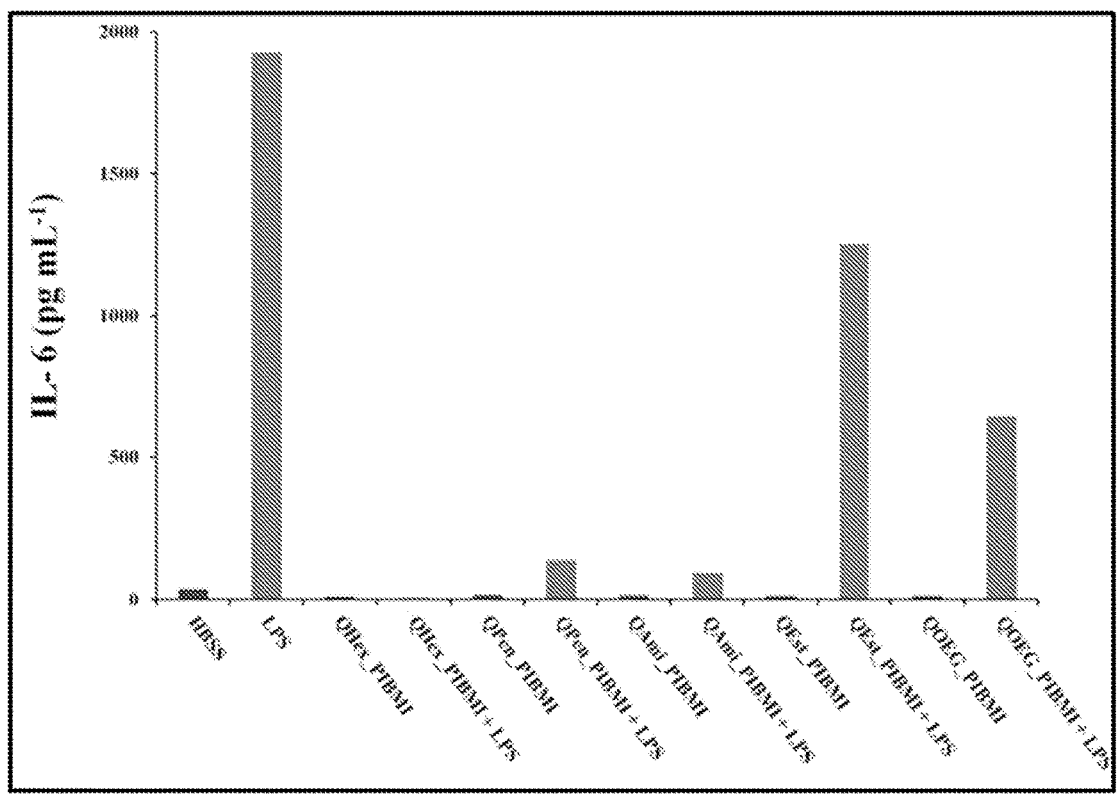

FIG. 13 provides graphical representation of in-vitro anti-inflammatory properties of the polymeric derivatives against human PBMCs. HBSS is used as vehicle control.

DETAILED DESCRIPTION OF INVENTION

To more clearly and concisely describe and point out the subject matter of the claimed invention, the following definitions are provided for specific terms, which are used in the following description and the appended claims.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

As used herein the term "aliphatic radical" refers to an organic radical having a valence of at least one comprising a linear or branched acyclic or non-aromatic cyclic array of atoms. The non-aromatic cyclic aliphatic radical may comprise one or more noncyclic components. For example, a cyclohexylmethyl group (C$_6$H$_{11}$CH$_2$—) is a cycloaliphatic radical which comprises a cyclohexyl ring (the array of atoms which is cyclic but which is not aromatic) and a methylene group (the noncyclic component). The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched acyclic or non-aromatic cyclic array of atoms" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C$_6$ aliphatic radical comprising a methyl group, the methyl group being a functional group which is an alkyl group. Similarly, the 4-nitrobut-1-yl group is a C$_4$ aliphatic radical comprising a nitro group, the nitro group being a functional group. Again, the prop-1-enyl radical (CH$_3$CH=CH—) is a C$_3$ aliphatic radical comprising an alkenyl group. Examples of non-aromatic cyclic radicals include but are not limited to steroids such as cholesterol and ergosterol. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Aliphatic radicals comprising one or more alkenyl groups may include octadec-9-enyl radical (CH$_3$(CH$_2$)$_7$CH=CH(CH$_2$)$_7$CH$_2$—), which is a C$_{18}$ aliphatic radical comprising single alkenyl group and octadec-9,12-dienyl radical (CH$_3$(CH$_2$)$_4$CH=CHCH$_2$CH=CH(CH$_2$)$_7$CH$_2$—), which is a C$_{18}$ aliphatic radical comprising two alkenyl groups. Further examples of aliphatic radicals include allyl (CH$_2$=CHCH$_2$—), propargyl (CH≡CCH$_2$—), aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e., —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilypropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, benzyl ($C_6H_5CH_2$—), naphthyl-1-methyl ($C_{10}H_7CH_2$—), anthracenyl-1-methyl ($C_{14}H_9CH_2$—) are aromatic radicals, which comprise a phenyl ring, a naphthyl ring, an anthracenyl ring (the aromatic group) respectively and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —OPhC($CF_3$)$_2$PhO—), 4-chloromethylphen-1-yl, 3-trifluorovinyl-2-thienyl, 3-trichloromethylphen-1-yl (i.e., 3-$CCl_3$Ph-), 4-(3-bromoprop-1-yl) phen-1-yl (i.e., 4-$BrCH_2CH_2CH_2$Ph-), and the like. Examples of aromatic radical include but are not limited to, tocopherol and tocotrienol. Further examples of aromatic radicals include 4-allyloxyphen-1-oxy, 4-aminophen-1-yl (i.e., 4-$H_2$NPh-), 3-aminocarbonylphen-1-yl (i.e., $NH_2$COPh-), 4-benzoylphen-1-yl, dicyanomethylidenebis (4-phen-1-yloxy) (i.e., —OPhC(CN)$_2$PhO—), 3-methylphen-1-yl, methylenebis(4-phen-1-yloxy) (i.e., —OPh$CH_2$PhO—), 2-ethylphen-1-yl, phenylethenyl, 3-formyl-2-thienyl, 2-hexyl-5-furanyl, hexamethylene-1,6-bis(4-phen-1-yloxy) (i.e., —OPh($CH_2$)$_6$PhO—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-$CH_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_7$—) represents a $C_7$ aromatic radical.

The term "hydrophobic" as used herein to describe a compound of the present invention or a substituent thereon, refers to the tendency of the compound or substituent thereon to lack an affinity for, to repel or to fail to absorb water, or to be immiscible in water. The term "hydrophobic" is not meant to exclude compounds or substituents thereon that are not completely immiscible in water.

For the purpose of the present invention, the terms "lipophilic" and "hydrophobic" may be used interchangeably.

The term "pharmaceutically acceptable salt" as used herein, refers to salts of the compounds that are substantially non-toxic to living organisms such that it could be effectively used for the treatment of a subject. For example, the pharmacokinetics and pharmcodynamics properties of a pharmaceutically acceptable salt may be suitable for in-vivo usage. Typical pharmaceutically acceptable salts of the compounds of the subject invention include those salts, which are prepared by reaction of the compounds of the present invention with a pharmaceutically acceptable mineral acid or organic acid. Such salts are classified as acid addition salts.

The term "treatment" as used herein includes any treatment of a condition or disease in a subject and includes: (i) preventing the disease or condition from occurring in a subject which may be predisposed to the disease but has not yet been diagnosed as having it; (ii) inhibiting the disease or condition, i.e. arresting its development; relieving the disease or condition, i.e. causing regression of the condition; or relieving the conditions caused by the disease, i.e. symptoms of the disease.

The term "effective amount" as used herein is a concentration at which an active ingredient optimally performs it intended use. For example, it is an amount that is effective to prevent a disease or condition from occurring in a subject and/or inhibit the disease or condition, i.e. arrest its development; relieve the disease or condition, i.e. cause regression of the condition; or relieve the conditions caused by the disease.

"Drug resistant bacterium" as used herein is a bacterium which is able to survive exposure to at least one drug. In some embodiments the drug resistant bacterium is a bacterium which is able to survive exposure to a single drug or multiple drugs. Examples of drug resistant bacterium include but are not limited to vancomycin resistant bacterium or methicilin resistant bacterium.

A "subject" used herein, refers to a multi-cellular living organism. For example, subject may be an animal that maybe a vertebrate or an invetebrate. In some embodiments the subject may be a mammal. In some embodiments the subject may be a human being.

The term "amphiphilic copolymer" means a copolymer which contains at least one hydrophilic domain and at least one hydrophobic domain.

The term "hydrophilic/lipophilic balance" means the ratio of the sum of the formula weights of the hydrophilic regions of a copolymer divided by the sum of the formula weights of the hydrophobic regions of the copolymer.

The term "micelle" includes without limitation micelles having shapes of spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "particle" includes, but is not limited to, nanoparticles. The shape of the particles can include without limitation spheres, cylinders, discs, needles, cones, vesicles, globules, rods, elipsoids, and any other shape that a micelle can assume under the conditions described herein, or any other shape that can be adopted through aggregation of the amphiphilic copolymers.

The term "nanoparticle" means a particle, the largest dimension of which is less than one micron.

The term "mean particle diameter" means the average value of the various diameters of regularly or irregularly shaped particles.

Particles of the present invention can be prepared in a variety of different ways. For example, one method of producing particles of the present invention comprises organizing the amphiphilic copolymers to produce a micellar assembly of the copolymers, The organizing step in these methods of preparation of particles of the invention can be performed in a number of different ways. For example, the amphiphilic copolymers can self-assemble by placing them in an appropriate concentration in a solvent system effective in orienting the amphiphilic copolymers into micelles. The appropriate concentrations in this step can be above the CAC of the compounds or below the CAC of the compounds or at the CAC of the compounds (See Example 8-10 below). The appropriate concentration of amphiphilic copolymers in this step can be from about 0.001 mg/mL to about 10 mg/mL, preferably from about 0.01 mg/mL to about 1 mg/mL, more preferably from about 0.1 mg/mL to about 0.5 mg/mL. Alternatively, active processes such as, for example, applying energy via heating, sonication, shearing, etc., can be employed to aid in orienting the amphiphilic copolymers forming the micelles.

The solvent system in these methods of preparation can predominantly comprise a hydrophilic solvent. For example the hydrophilic solvent system can be selected from the group consisting of acetaldehyde, acetic acid, acetone, aniline, benzyl alcohol, butanol, chloroethanol, cyclohexanol, di(ethylene glycol), diglyme, N,N-dimethylformamide, dimethylsulfoxide, dioxane, ethanol, ehtylene glycol, formamide, hexa (ethylene glycol), methanol, methyl acetate, 2-methyl-1-propanol, nitromethane, octanol, penta(ethylene glycol), pentanol, picoline, propanol, isopropanol, pyridine, tetrahydrofuran, tetra (ethylene glycol), tri(ethylene glycol), water, and the like, and mixtures thereof.

Preferably, the hydrophilic solvent system predominantly comprises water.

Preferably, a mixture of solvents comprises water and hydrophobic solvent or combinations thereof.

Alternatively, the solvent system can predominantly comprise a hydrophobic solvent. For example the hydrophobic solvent system can be an alkane, an alkene, an aromatic solvent, an aliphatic solvent, a chlorinated solvent, an aldehyde, a ketone, a nitrile, an ester, an alcohol, an aniline, a sulfide, an ether, a siloxane, a silane, a heterocycle, or the like, and combinations thereof. For example, the hydrophobic solvent can be acetaldehyde, acetone, acetonitrile, acetyl acetone, amyl acetate, n-amyl alcohol, tert-amyl alcohol, aniline, benzene, 2-butanone, butyl acetate, butyl benzene, butylcyclohexane, carbon disulfide, carbon tetrachloride, chlorobenzene, ehlorobutane, chloroform, ehloromethane, chloropropane, chloropentane, chlorotoluene, cumene, cycloheptane, cyclohexane, cyclohexanol, cyclohexanone, cyclohexene, cyclooctane, cyclopentane, decahydronaphthalene, decene, decnol, dichlorobenzene, dichloroethane, dichloromethane, diglyme, N,N-dimethylfomramide, 2,6-dimethyl-4-heptnaone, dimethylhexane, dimethylpentane, dimethylpropane, dimethylsulfoxide, dioxane, dodecane, ethyl acetate, ethyl benzene, ethyl ether, ethylpentane, fluorobenzene, glyme, heptane, heptanol, heptanone, hexamethyldisiloxane, hexane, hexadecane, hexanol, hexanone, isoamyl acetate, isopropyl ether, mesitylene, methylbutane, methylcyclohexane, methylheptane, methylhexane, methylpentane, 4-methyl-2-pentanone, methylpropane, N-methylpyrrolidinone, naphthalene, nitrobenzene, nitroethane, nonane, octane, octanone, pentane, picoline, propylacetate, tetrachloroethylene, tetradecane, tetrahydrofuran, tetrahydronaphthalene, tetramethylhexane, toluene, trichloroethane, trichloroethylene, trimethylpentane, undecane, xylene, or the like, and combinations thereof.

It should be noted that the terms "hydrophilic" and "hydrophobic" as applied to solvents herein are relative. This is to say that any particular solvent, or combination of solvents, can be "hydrophilic" or "hydrophobic" depending upon the particular amphiphilic copolymer region under consideration.

The particles of the present invention can assume a variety of shapes, including spheres, cylinders, discs, needles, cones, vesicles, globules, rods, elipsoids, and any other shape that a micelle can assume under the conditions described herein, or any other shape that can be adopted through aggregation of the amphiphilic copolymers.

The size of the particles can be larger than a micron, although sizes less than a micron are preferred. When the particles take the form of spheres, they can have a mean particle diameter from about 2 nm to about 1000 nm, preferably from about 5 nm to about 800 nm, more preferably from about 10 nm to 500 nm. When the particles take the form of cylinders or discs, they can have an aspect ratio from about 0.5 to about 5,000, preferably from about 1 to about 500, more preferably from about 2 to about 50, still more preferably from about 2 to about 25.

"Systemic inflammatory response syndrome," or "SIRS," refers to a clinical response to a variety of severe clinical insults, as manifested by two or more of the following conditions within a 24-hour period: body temperature greater than 38° C. (100.4° F.) or less than 36° C. (96.8° F.); heart rate (HR) greater than 90 beats/minute; respiratory rate (RR) greater than 20 breaths/minute, or $P_{CO2}$ less than 32 mm Hg, or requiring mechanical ventilation; and white blood cell count (WBC) either greater than $12.0 \times 10^9$/L or less than $4.0 \times 10^9$/L or having greater than 10% immature forms (bands).

These symptoms of SIRS represent a consensus definition of SIRS that may be modified or supplanted by an improved definition in the future. The present definition is used to clarify current clinical practice and does not represent a critical aspect of the invention.

A subject with SIRS has a clinical presentation that is classified as SIRS, as defined above, but is not clinically deemed to be septic.

"Sepsis" refers to a SIRS-positive condition that is associated with a confirmed infectious process. Clinical suspicion of sepsis arises from the suspicion that the SIRS-positive condition of a SIRS subject is a result of an infectious process.

"Suppressing a potentially harmful inflammation" as used herein means that the compounds or the compositions thereof of the present invention are able to down-regulate, in mammalian cells, genes and molecules that are natural components of the innate immune response and assist in the resolution of infections without excessive increases of pro-inflammatory cytokines like interleukins (IL-6) or TNFα which can cause potentially harmful inflammation and thus stimulate a sepsis reaction in a subject.

"Cell-based assays" for inhibitors and activators include, e.g., applying putative modulator compounds to a cell expressing a receptor, e.g., surface receptors, and then determining the functional effects on receptor signaling, as described herein. Cell-based assays or include, but are not limited to, in vivo tissue or cell samples from a mammalian subject or in vitro cell-based assays comprising a receptor that are treated with a potential activator, inhibitor, or modulator are compared to control samples without the inhibitor, activator, or modulator to examine the extent of inhibition. These assays include binding assays, for example, radioligand or fluorescent ligand binding assays to cells, plasma membranes, detergent-solubilized plasma membrane proteins, immobilized collagen Control samples (untreated with inhibitors) can be assigned a relative activity value of 100%. Inhibition of a receptor is achieved when the receptor activity value relative to the control is about 80%, optionally 50% or 25-0%.

"Innate immunity" as used herein refers to the natural ability of an organism to defend itself against invasions by pathogens. Pathogens or microbes as used herein, can include, but are not limited to bacteria, fungi, parasites, and viruses. Innate immunity is contrasted with acquired/adaptive immunity in which the organism develops a defensive mechanism based substantially on antibodies and/or immune lymphocytes that is characterized by specificity, amplifiability and self vs. non-self discrimination. With innate immunity, broad, nonspecific immunity is provided and there is no immunologic memory of prior exposure. The hallmarks of innate immunity are effectiveness against a broad variety of potential pathogens, independence of prior exposure to a pathogen, and immediate effectiveness (in contrast to the specific immune response which takes days to weeks to be elicited). In addition, innate immunity includes immune responses that affect other diseases, such as cancer, inflammatory diseases, multiple sclerosis, various viral infections, and the like. In innate immunity, the immune response is not dependent upon antigens. The innate immunity process can include the production of secretory molecules and cellular components as set forth above. In innate immunity, the pathogens are recognized by receptors (for example, Toll-like receptors) that have broad specificity, are capable of recognizing many pathogens, and are encoded in the germline. These Toll-like receptors have broad specificity and are capable of recognizing many pathogens. When cationic peptides are present in the immune response, they aid in the host response to pathogens. This change in the immune response induces the release of chemokines, which promote the recruitment of immune cells to the site of infection.

In some embodiments a compound of Formula I is provided:

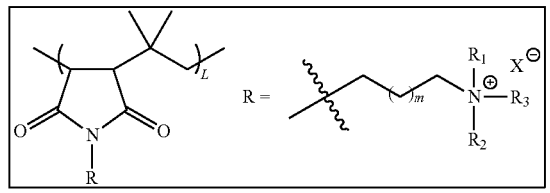

Formula I wherein,

'm' is an integer ranging from 0 to 1

'L' is an integer ranging from 1 to 100

$R_1$, $R_2$ and $R_3$ are, independently at each occurrence, a hydrogen atom or methyl radical or $C_2$-$C_{40}$ aliphatic radical or $C_3$-$C_{40}$ aromatic radical or combinations thereof.

'X' is selected from a group consisting of chloride, bromide, iodide, salicylate, 4-aminosalicylate, phosphomycin ((−)-(1R,2S)-(1,2-Epoxypropyl)phosphonate) and terephthalate.

The integer m includes, but not limited to 0 and 1. In some embodiments, when m is integer 0, the R moiety in the Formula I is —$CH_2CH_2N^+R_1R_2R_3$ and when m is integer 1, the R moiety in the Formula I is —$CH_2CH_2CH_2N^+R_1R_2R_3$.

L is an integer. In some embodiments, L is ranging from 1 to 100. In some other embodiments, L is ranging from 10 to 40. For example, L is an integer 39.

In some embodiments $R_1$, $R_2$, and $R_3$ includes a structural moiety comprising 1 to 40 carbon atoms. $R_1$, $R_2$, and $R_3$ may be aliphatic radical including noncyclic linear, branched or non-aromatic cyclic array of atoms. For example $R_1$, $R_2$, and $R_3$ may be H—, $CH_3$—, $CH_3CH_2$—, $CH_3(CH_2)_n$— where n is an integer ranging from 2 to 39. In some embodiments $R_1$, $R_2$, and $R_3$ may include one or more alkenyl or alkynyl groups. Examples include but are not limited to, octadec-9-enyl ($CH_3(CH_2)_7CH$=$CH(CH_2)_7CH_2$—), which is a $C_{18}$ aliphatic structural moiety comprising single alkenyl group and octadec-9,12-dienyl radical ($CH_3(CH_2)_4CH$=$CHCH_2CH$=$CH(CH_2)_7CH_2$—), which is a $C_{18}$ aliphatic radical comprising two alkenyl groups. In some other embodiments, $R_1$, $R_2$, and $R_3$ may have one or more heteroatoms such as nitrogen, sulfur, silicon, selenium and oxygen. In some embodiments $R_1$, $R_2$, and $R_3$ may include a wide range of structural moieties such as haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example $R_1$, $R_2$, or $R_3$ may be:

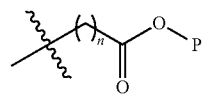

wherein, P is a $C_1$-$C_{24}$ aliphatic saturated radical or a $C_2$-$C_{24}$ aliphatic unsaturated radical, and n is an integer ranging from 1 to 4,

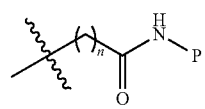

wherein, P is a $C_1$-$C_{24}$ aliphatic saturated radical or a $C_2$-$C_{24}$ aliphatic unsaturated radical, and n is an integer ranging from 1 to 4,

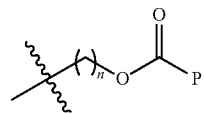

wherein, P is a $C_1$-$C_{24}$ aliphatic saturated radical or a $C_2$-$C_{24}$ aliphatic unsaturated radical, and n is an integer ranging from 1 to 4,

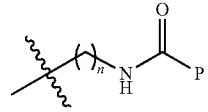

wherein, P is a $C_1$-$C_{24}$ aliphatic saturated radical or a $C_2$-$C_{24}$ aliphatic unsaturated radical, and n is an integer ranging from 1 to 4,

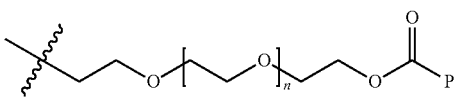

wherein, P is a $C_1$-$C_{24}$ aliphatic saturated radical or a $C_2$-$C_{24}$ aliphatic unsaturated radical, and n is an integer ranging from 0 to 3,

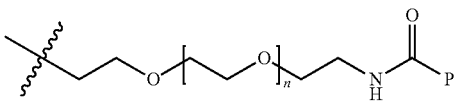

wherein, P is a $C_1$-$C_{24}$ aliphatic saturated radical or a $C_2$-$C_{24}$ aliphatic unsaturated radical, and n is an integer ranging from 0 to 3,

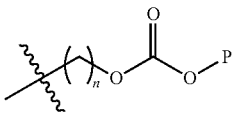

wherein, P is a $C_1$-$C_{24}$ aliphatic saturated radical or a $C_2$-$C_{24}$ aliphatic unsaturated radical, and n is an integer ranging from 1 to 4,

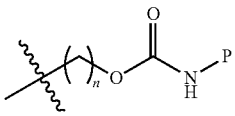

wherein, P is a $C_1$-$C_{24}$ aliphatic saturated radical or a $C_2$-$C_{24}$ aliphatic unsaturated radical, and n is an integer ranging from 1 to 4,

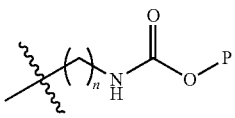

wherein, P is a $C_1$-$C_{24}$ aliphatic saturated radical or a $C_2$-$C_{24}$ aliphatic unsaturated radical, and n is an integer ranging from 1 to 4, and

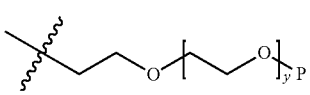

wherein, P is a $C_1$-$C_{24}$ aliphatic saturated radical or a $C_2$-$C_{24}$ aliphatic unsaturated radical, and y is an integer ranging from 0 to 3.

In some embodiments P includes an aliphatic saturated radical comprising 1 to 24 carbon atoms. P may include noncyclic linear, branched or non-aromatic cyclic array of atoms. For example P may be $CH_3$—, $CH_3CH_2$—, or $CH_3(CH_2)_n$— where n is an integer ranging from 2 to 23. In some embodiments P may include aliphatic unsaturated radical comprising 2 to 24 carbon atoms. P may include one or more alkenyl or alkynyl groups. Examples of aliphatic unsaturated radical include but are not limited to $CH_3(CH_2)_7CH=CH(CH_2)_6CH_2$—, which is an aliphatic structural moiety comprising single alkenyl group and $CH_3(CH_2)_4CH=CHCH_2CH=CH(CH_2)_6CH_2$—, which is an aliphatic radical comprising two alkenyl groups.

In some embodiments $R_1$, $R_2$, and $R_3$ may include an aromatic radical having an array of atoms having a valence of at least one comprising at least one aromatic group. The aromatic group may include heteroatoms such as nitrogen, sulfur, selenium, silicon and oxygen, or may be composed exclusively of carbon and hydrogen. Examples of aromatic radical include but are not limited to phenyl, pyridyl, furanyl, thienyl, naphthyl, anthryl, phenylene, and biphenyl radicals. The aromatic radical may also include nonaromatic components. For example, benzyl ($C_6H_5CH_2$—), naphthyl-1-methyl ($C_{10}H_7CH_2$—), anthracenyl-1-methyl ($C_{14}H_9CH_2$—) are aromatic radicals, which comprise a phenyl ring, a naphthyl ring, an anthracenyl ring (the aromatic group) respectively and a methylene group (the non-aromatic component). In some embodiments, aromatic radical may include a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is an aromatic radical comprising a methyl group, the methyl group being a functional group which is an alkyl group. Similarly, the 2-nitrophenyl group is an aromatic radical comprising a nitro group. Aromatic radicals may include halogenated aromatic radicals.

In some embodiments $R_1$, $R_2$ and $R_3$ may be a "hydrophobic moiety" comprising noncyclic linear, branched or cyclic array of atoms with at least six carbon atoms. In some embodiments the "hydrophobic moiety" may include an aromatic radical. In one aspect of this embodiment said hydrophobic moiety comprises more than 6 and up to 40 carbon atoms. In a second aspect said hydrophobic moiety comprises between 6 and 24 carbon atoms and in a third aspect said hydrophobic moiety comprises between 8 and 14 carbon atoms. In some embodiments said hydrophobic moiety may include one or more heteroatoms such as nitrogen, sulfur, silicon, selenium and oxygen. In one embodiment said hydrophobic moiety may include one or more alkenyl or alkynyl groups. In other embodiments said hydrophobic moiety may include a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. In some embodiments the branching of the main chain of said hydrophobic moiety may comprise small building blocks. Preferred building blocks comprise methyl-, ethyl-, propyl-, isopropyl-, methoxy-, ethoxy-, methoxymethyl-, ethoxymethyl-, methoxyethyl-, ethoxyethyl- and vinyl- or halogen groups or mixtures thereof. Alternatively, said hydrophobic moiety may include sterols, said sterols may further include functional groups.

In the compound of Formula I, $R_1$, $R_2$, and $R_3$ are independently selected from an aliphatic radical or an aromatic radical. In some embodiments $R_1$, $R_2$, and $R_3$ may all be different radicals; for example, $R_1$ may be methyl radical ($CH_3$—), $R_2$ may be ethyl radical ($CH_3CH_2$—) and $R_3$ may be propyl radial ($CH_3CH_2CH_2$—). In some embodiments, $R_1$ and $R_2$ may be a same radical and $R_3$ may be a different radical from $R_1$ and $R_2$; for example $R_1$ and $R_2$ may be a methyl radical ($CH_3$—), and $R_3$ may be ethyl radical ($CH_3CH_2$—). In some embodiments $R_1$ and $R_3$ may be a same radical and $R_2$ may be a different radical from $R_1$ and $R_3$; for example $R_1$ and $R_3$ may be a methyl radical ($CH_3$—), and $R_2$ may be an ethyl radical ($CH_3CH_2$—). In some embodiments $R_2$ and $R_3$ may be a same radical and $R_1$ may be a different radical from $R_2$ and $R_3$; for example $R_2$ and $R_3$ may be a methyl radical ($CH_3$—), and $R_1$ may be an ethyl radical ($CH_3CH_2$—). In some embodiments $R_1$, $R_2$, and $R_3$ may all be a same radical; for example $R_1$, $R_2$, and $R_3$ may be an ethyl radical ($CH_3CH_2$—).

In some embodiments a compound of Formula II is provided:

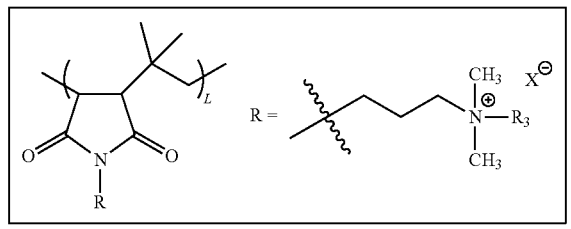

Formula II wherein, $R_3$ is a hydrogen atom or $C_1$-$C_{10}$ aliphatic radical, L is an integer 39 and X is a bromide.

In some embodiments $R_3$ may include H—, $CH_3(CH_2)_1$—, $CH_3(CH_2)_3$—, $CH_3(CH_2)_4$—, $CH_3(CH_2)_5$—, $CH_3(CH_2)_6$—, $CH_3(CH_2)_7$—, $CH_3(CH_2)_9$—, $CH_3(CH_2)_2OCOCH_2$—, $CH_3(CH_2)_2NHCOCH_2$—, or $CH_3O(CH_2)_2O(CH_2)_2$—.

In some embodiments, a pharmaceutically acceptable salt of the compounds of the present invention with a pharmaceutically acceptable mineral acid or organic acid include hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, trifluoroacetic acid, salicylic acid, terephthalic acid and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, trifluoroacetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methanesulfonate, propanesulfonate, naphthalene-1-sulfonate, naphthalene-2-sulfonate, mandelate, chloride, bromide, iodide, salicylate, 4-aminosalicylate, phosphomycin ((-)-(1R,2S)-(1,2-Epoxypropyl)phosphonate) and terephthalate and the like.

In some embodiments, a pharmaceutically acceptable salt of the compounds of the present invention may be with a pharmaceutically acceptable organic acid such as hydrobromic acid and the pharmaceutically acceptable salt may be bromide.

It should be recognized that the particular counterion forming a part of any salt of this invention may not be of a critical nature, so long as the salt as a whole is pharmacologically acceptable and as long as the counterion does not contribute undesired qualities to the salt as a whole.

In some embodiments, the "composition" may be a composition comprising drug along with conventional pharmaceutical carriers. In some other embodiments, the excipients formulated for immediate or sustained release. Other time-release profiles, such as combinations of immediate and sustained release are also possible. As used herein, the term "pharmaceutically carrier and/or excipient" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray, or a liquid aerosol or dry powder formulation for inhalation.

Liquid dosage forms for oral administration include pharmaceutically acceptable emulsions, microemulsions, liposome, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, any oil including mono- or diglycerides or fatty acids such as oleic acid can be used in the preparation of injectables.

In order to prolong the effect of a drug, it is often desirable to slow the release of the drug. Slow release of the drug can be accomplished by dissolving or suspending the drug in an oil vehicle. Injectable depot forms can be made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions which are compatible with body tissues. Alternatively, the compounds of this invention can be conjugates covalently, encapsulated, or adsorbed onto carbon nanospheres or nanotubes to form slow release compositions.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions which can be used include polymeric substances and waxes.

The active compounds can also be in micro-encapsulated form with one or more excipients as noted above. The solid dosage forms of tablets, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Compositions of the invention may also be formulated for delivery as a liquid aerosol or inhalable dry powder. Liquid aerosol formulations may be nebulized predominantly into particle sizes that can be delivered to the terminal and respiratory bronchioles where bacteria reside in patients with bronchial infections, such as chronic bronchitis and pneumonia.

Compounds of the invention may also be formulated for use as topical powders and sprays that can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Alternatively, the compound or the pharmaceutical composition thereof, can also be coated or impregnated into catheters or stents for local drug delivery.

In one embodiment a method of making a compound of formula I and formula II is disclosed. The method includes reacting 3-aminopropyldimethylamine with a solution of poly (isobutylene-alt-maleic anhydride) (PIBMA) in dimethyl formamide to obtain poly (isobutylene-alt-N—(N',N'-dimethylaminopropyl)-maleimide) (PIBMI); reacting PIBMI obtained in previous step with bromoaliphatic or bromoaromatic compounds including but not limited to bromoalkane, 1-bromo-2(2-methoxyethoxy) ethane, propyl-1-bromoethanoate, or N-propyl-1-bromoethanamide in dimethylformamide/chloroform to obtain a solution; cooling and precipitating the solution obtained with n-hexane or diethylether to obtain the compounds in formula 1 or Formula II.

The R moiety comprises a structural moiety of general formula:

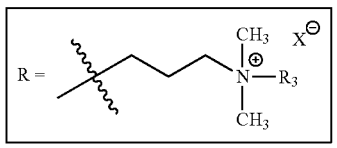

wherein,

R$_3$ is, independently at each occurrence, a hydrogen atom or methyl radical or C$_2$-C$_{40}$ aliphatic radical or C$_3$-C$_{40}$ aromatic radical or combinations thereof.

'X' is selected from a group consisting of chloride, bromide, iodide, salicylate, 4-aminosalicylate, phosphomycin ((−)-(1R,2S)-(1,2-Epoxypropyl)phosphonate) and terephthalate.

Examples of R moiety include but are not limited to,
HN$^+$(CH$_3$)$_2$CH$_2$CH$_2$CH$_2$—,
CH$_3$N$^+$(CH$_3$)$_2$CH$_2$CH$_2$CH$_2$—,
CH$_3$(CH$_2$)$_1$N$^+$(CH$_3$)$_2$CH$_2$CH$_2$CH$_2$—,
CH$_3$(CH$_2$)$_3$N$^+$(CH$_3$)$_2$CH$_2$CH$_2$CH$_2$—,
CH$_3$(CH$_2$)$_4$N$^+$(CH$_3$)$_2$CH$_2$CH$_2$CH$_2$—,
CH$_3$(CH$_2$)$_5$N$^+$(CH$_3$)$_2$CH$_2$CH$_2$CH$_2$—,
CH$_3$(CH$_2$)$_6$N$^+$(CH$_3$)$_2$CH$_2$CH$_2$CH$_2$—,
CH$_3$(CH$_2$)$_7$N$^+$(CH$_3$)$_2$CH$_2$CH$_2$CH$_2$—,
CH$_3$(CH$_2$)$_9$N$^+$(CH$_3$)$_2$CH$_2$CH$_2$CH$_2$—,
CH$_3$(CH$_2$)$_2$OCOCH$_2$N$^+$(CH$_3$)$_2$CH$_2$CH$_2$CH$_2$—,
CH$_3$(CH$_2$)$_2$NHCOCH$_2$N$^+$(CH$_3$)$_2$CH$_2$CH$_2$CH$_2$—,
CH$_3$O(CH$_2$)$_2$O(CH$_2$)$_2$N$^+$(CH$_3$)$_2$CH$_2$CH$_2$CH$_2$—,
CH$_3$(CH$_2$)$_7$CH=CH(CH$_2$)$_7$CH$_2$N$^+$(CH$_3$)$_2$CH$_2$CH$_2$CH$_2$—,
CH$_3$(CH$_2$)$_4$CH=CHCH$_2$CH=CH(CH$_2$)$_7$CH$_2$N$^+$(CH$_3$)$_2$CH$_2$CH$_2$CH$_2$—,
CH$_3$(CH$_2$)$_7$OCOCH$_2$N$^+$(CH$_3$)$_2$CH$_2$CH$_2$CH$_2$—,
CH$_3$(CH$_2$)$_7$NHCOCH$_2$N$^+$(CH$_3$)$_2$CH$_2$CH$_2$CH$_2$—,
CH$_3$(CH$_2$)$_7$CH=CH(CH$_2$)$_6$COOCH$_2$CH$_2$CH$_2$N$^+$(CH$_3$)$_2$CH$_2$CH$_2$CH$_2$—,
or CH$_3$(CH$_2$)$_7$CH=CH(CH$_2$)$_6$CONHCH$_2$CH$_2$CH$_2$N$^+$(CH$_3$)$_2$CH$_2$CH$_2$CH$_2$—.

The compounds of the present invention, or pharmaceutically acceptable salts or compositions thereof can be formulated for any conventional means of delivery, including oral or parenteral delivery for the therapeutic or prophylactic treatment of infectious diseases, preferably bacterial diseases. The bacterial diseases which may be therapeutically or prophylactically treated with the compounds and/or formulations of the present invention include those caused by Gram-positive and/or Gram-negative microorganisms.

The compounds of the present invention may be administered separately or in combination with any other drug or therapeutic agent. Examples of other therapeutic agents and/or drugs that can be administered with the compounds and/or formulations of the present invention include, but are not limited to, beta lactam antibiotics, such as penems, penams, cephems, carbapenems, oxacephems, carbacephems, and monobactams, or other antibiotics such as cycloserine and fosfomycin. The other therapeutic agent need not be an antibiotic.

The compound and/or composition are administered to the subject in a therapeutically effective amount. Thus, the compound of the present invention can be administered to the subject, preferably a human, in an amount ranging from about 0.25 to about 2 grams per day. The compound and/or composition of the present invention can be administered in a single daily dosage or in multiple doses per day. Other periodic treatment protocols may also be adopted. Thus, the treatment protocol may require administration over extended periods of time, e.g., for several days or for from about one to six weeks. The therapeutically effective amounts of the compound of the invention discussed above are merely exemplary. Thus, the amount per administered dose or the total amount administered will depend on such factors as the nature and severity of the infection, the age and general health of the patient, the tolerance of the patient to the compounds and/or formulations of the present invention and the microorganism or microorganisms involved in the infection.

In some embodiments, treatment includes preventing a disease or condition from occurring in a subject which may be predisposed to the disease but has not yet been diagnosed as having it. In some other embodiments, treatment includes inhibiting the disease or condition, i.e. arresting its development; relieving the disease or condition, i.e. causing regression of the condition; or relieving the conditions caused by the disease, i.e. symptoms of the disease.

In the present invention, the desired therapeutic effect would be treatment of a disease condition resulting from gram positive, gram negative, or acid fast bacterial infections. These include but are not limited to diseases such as infective endocarditis, skin infections, meningitis, urinary tract infections, gastrointestinal infections, respiratory tract infections etc caused by pathogenic bacteria such as Staphylococci, Streptococci, *Haemophilus, Moraxalla, Chlamydia, Rickettsiae, Mycoplasm, Legionella, Mycobacterium, Helicobacter, Clostridium, Bacteroides, Propionibacterium* acnes, *Corynebacterium, Bacillus* or *Enterobactericeae* etc.

In some embodiments, bacterial infections may be caused by drug sensitive bacteria, or drug resistant bacteria. In some other embodiments, infections may caused by drug sensitive bacteria, which later become drug resistant once inside the body of the infected host. In some embodiments, infections may be caused by both drug sensitive bacteria and drug resistant bacteria.

In some embodiments, drug sensitive bacteria may include but are not limited to Staphylococci, Streptococci, Enterococci, *Haemophilus, Moraxalla, Chlamydia, Rickettsiae, Mycoplasm, Legionella, Mycobacterium, Helicobacter, Clostridium, Bacteroides, Propionibacterium* acnes, *Corynebacterium, Bacillus* or *Enterobactericeae* etc.

In some other embodiments, drug resistant bacteria may include but are not limited to methicilin resistant *S. aureus* (MRSA), vancomycin resistant *E. faecalis*, vancomycin resistant *E. faecium*.

In some other embodiments, bacterium is selected from a group consisting of *Escherichia coli, Staphylococcus aureus, Pseudomonas aeruginosa, Klebsiella pneumoniae, Enterococcus faecium* methicillin resistant *Staphylococcus aureus* and vancomycin resistant *Enterococcus faecium*.

Compound or the compositions thereof of the present invention can suppress potentially harmful inflammation comprising administering to a subject suffering from sepsis.

Particularly, compound or the compositions thereof of the present invention can also counteract some of the more harmful aspects of inflammation (e.g. sepsis) which is extremely important since rapid killing of bacteria and subsequent liberation of bacterial components such as lipopolysaccharide (LPS) or lipotechoic acid (LTA) or peptidoglycan can induce fatal conditions.

The invention further provides a method of suppressing a potentially harmful inflammation comprising contacting a cell containing a gene that encodes a polypeptide involved in inflammation and sepsis with the compound or the compositions thereof of the present invention, wherein the expression of the gene is modulated in the presence of the compound compared with expression in the absence of compound.

In some aspects, the compound or the compositions thereof of the present invention inhibits the inflammatory or septic response.

In other aspects, the compound or the compositions thereof of the present invention blocks the inflammatory or septic response.

In other aspects, the compound or the compositions thereof of the present invention inhibits the expression of a proinflammatory gene or molecule.

In some such aspects the compound or the compositions thereof of the present invention inhibits the expression of interleukins (IL-6) or TNF-α.

In some aspects, the inflammation is induced by a microbe or microbial ligand acting on a Toll-like receptor. In some such aspects, the microbial ligand is a bacterial endotoxin or lipopolysaccharide.

The compounds or the compositions thereof of the present invention do not stimulate a septic reaction. The compounds or the compositions thereof of the present invention also possess anti-sepsis activity including an ability to reduce the expression of IL-6 or TNFα in response to bacterial ligands like LPS or LTA.

In one aspect, the present invention provides the use of compounds or the compositions thereof of the present invention to reduce sepsis and inflammatory responses by acting directly on host cells. In this aspect, a method of identification of a polynucleotide or polynucleotides that are regulated by one or more sepsis or inflammatory inducing agents is provided, where the regulation is altered by compounds or the compositions thereof of the present invention. Such sepsis or inflammatory inducing agents include, but are not limited to endotoxic lipopolysaccharide (LPS), lipoteichoic acid (LTA) and/or CpG DNA or intact bacteria or other bacterial components. The identification is performed by contacting the host cell with the sepsis or inflammatory inducing agents and further contacting with a cationic peptide either simultaneously or immediately after. The expression of the polynucleotide or polypeptide in the presence and absence of the compounds or the compositions thereof of the present invention is observed and a change in expression is indicative of a polynucleotide or polypeptide or pattern of polynucleotides or polypeptides that is regulated by a sepsis or inflammatory inducing agent and inhibited by compounds or the compositions thereof of the present invention.

As can be seen in Example 16 below, compounds or the compositions thereof of the present invention have an ability to alter the expression of polynucleotides or polypeptides regulated by LPS, particularly the quintessential pro-inflammatory cytokine IL-6. High levels of endotoxin in the blood are responsible for many of the symptoms seen during a serious infection or inflammation such as fever and an elevated white blood cell count, and many of these effects reflect or are caused by high levels of induced IL-6. Endotoxin (also called lipopolysaccharide) is a component of the cell wall of Gram-negative bacteria and is a potent trigger of the pathophysiology of sepsis. The basic mechanisms of inflammation and sepsis are related.

In some embodiments, a subject refers to a multi-cellular living organism. For example, subject may be an animal that may be a vertebrate or a inverterbate. In some embodiments the subject may be a mammal. In some embodiments the subject may be a human being.

In some embodiments, an article comprising a composition comprising the compound of the present invention or pharmaceutically acceptable salt thereof, include but are not limited to medical implants, catheters, or stents. For example, the compound of the present invention or pharmaceutically acceptable salt thereof may be coated on or impregnated into the medical implants, catheters, or stents.

EXAMPLES

The following examples provide details concerning the synthesis, properties, activities, and applications of the compounds of the present invention. It should be understood the following is representative only, and that the invention is not limited by the details set forth in these examples.

Materials and Instrumentation

All the solvents are of reagent grade and dried prior to use wherever required. Bromoacetyl-bromide, poly(isobutylene-alt-maleic anhydride) (typical Mw=6000 g/mol), 3-aminopropyldimethylamine, 1-Propyl amine and 1-bromo-2(2-methoxyethoxy)ethane are purchased from Sigma-Aldrich (India) and used as received. 1-bromo ethane, 1-bromo butane and 1-bromo octane are purchased from Avra chemicals (India) and 1-propanol and 1-bromo hexane are obtained from Spectrochem (India) respectively and used as received. Dialysis membrane-150 with a molecular weight cut off of 10 KDa is obtained from HIMEDIA (India). Dialysis tubing, benzoylated with NMWCO of 2 KDa is purchased from Sigma-Aldrich (India). NMR spectra are recorded using Bruker AMX-400 (400 MHz for $^1$H and 100 MHz for $^{13}$C) spectrometer. The chemical shifts (δ) are reported in parts per million downfield from the peak for the internal standard TMS for $^1$H NMR and $^{13}$CNMR. Infrared (IR) spectra of the solid compounds are recorded on Bruker IFS66 V/s spectrometer using KBr pellets. IR spectra of the compounds soluble in low-boiling solvents are recorded with the same instrument using NaCl crystal. Fluorescence studies are done using Perkin Elmer LS 55 spectrometer. Optical density is measured by Tecan InfinitePro series M200 Microplate Reader. SEM images are obtained using Quanta 3D FEG (FEI) field emission scanning electron microscope. Bacterial strains, *P. aeruginosa* (MTCC 424), *S. aureus* (MTCC 737) and *E. coli* (MTCC 443) are purchased from MTCC (Chandigarh, India). *E. faecium* (ATCC 19634), β-lactamase producing and drug-resistant *K. pneumoniae* (ATCC 700603), MRSA (ATCC 33591), vancomycin resistant *E. faecium* (VRE) ((OrlaJensen) Schleifer and Kilpper-Balz, ATCC 51559) are obtained from ATCC (Rockville, Md.).

Example: 1

Figure 1:
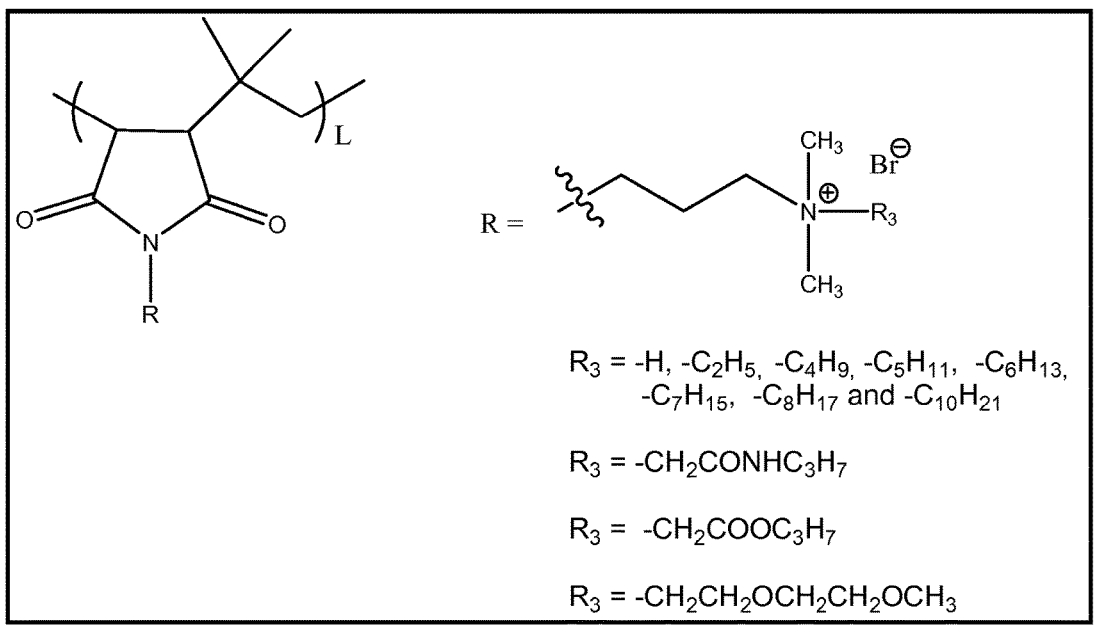
Figure 2:
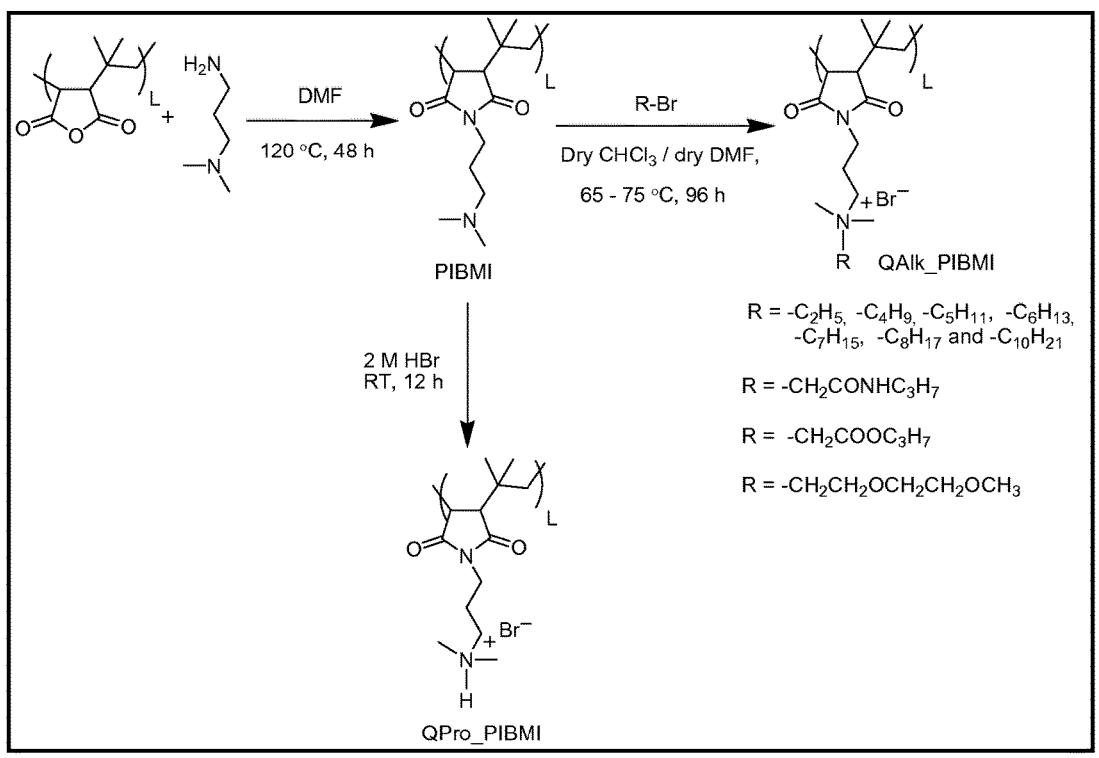
FIG. 2 shows the general synthetic route for the synthesis of PIBMI derivatives.
Figure 3:
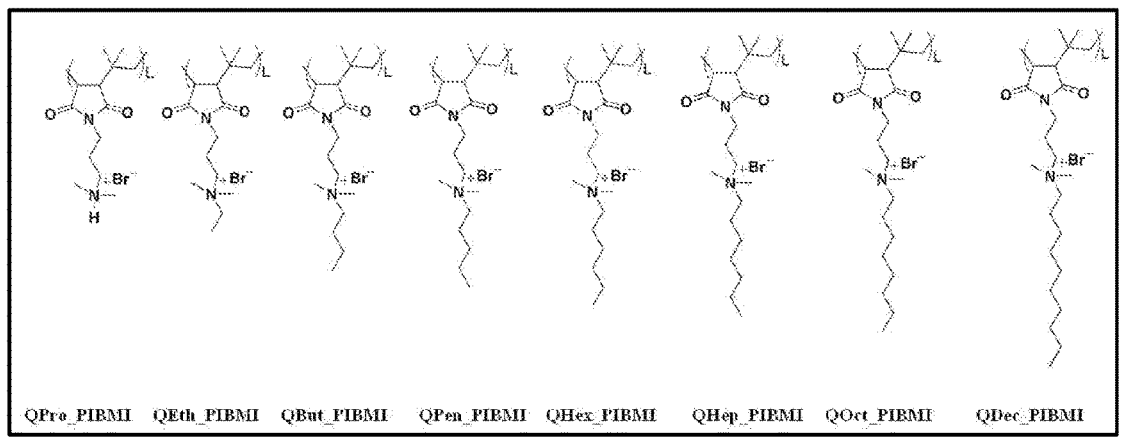
FIG. 3 shows the exact structures of QPro_PIBMI and QAlk_PIBMI derivatives with n-alkyl side chains.
Figure 4:
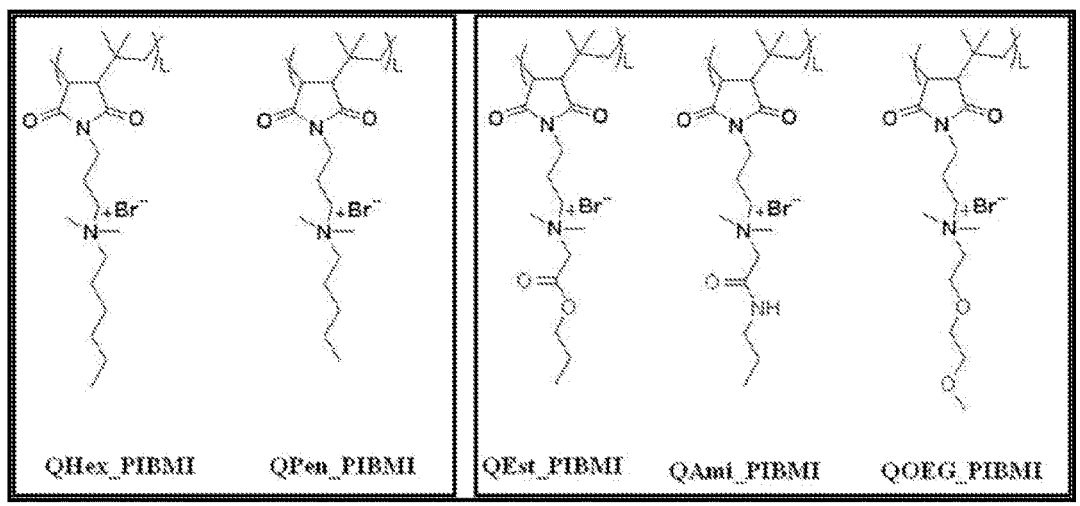
FIG. 4 shows exact structures of the quaternized amphiphilic PIBMI derivatives containing (A) hexyl and pentyl side chains and (B) side chains amide, ester and ether moieties.

A series of water soluble cationic alternating copolymers are synthesized based on quaternized poly (isobutylene-alt-N—(N',N'-dimethyl N'-alkyl aminopropyl)-maleimide) (PIBMI) using facile synthetic methodologies from commercially available poly(isobutylene-alt-maleic anhydride). Simple functionalization of the polymer backbone based on highly reactive anhydride ring with 3-aminopropyldimethylamine gives poly (isobutylene-alt-N—(N',N'-dimethylaminopropyl)-maleimide) followed by quaternization with different alkylating agents yielding the corresponding quaternized PIBMI derivatives in a simple two-step process. The general synthetic route of the compounds (FIGS. 1 and 3-4) is presented in FIG. 2. The steps employed in the method of synthesising cationic moeity represented in FIG. 2 is further elaborated below. The quaternized polymeric derivatives are denoted according to the type of alkylating agent used. QAlk_PIBMI, QAmi_PIBMI, QEst_PIBMI, QOEG_PIBMI represent the PIBMI derivatives quaternized with alkylating agents containing different alkyl, amide, ester and oligo ethylene glycol moieties respectively (FIGS. 3-4).

Synthesis of poly(isobutylene-alt-N—(N',N'-dimethylaminopropyl)-maleimide)-PIBMI To a solution of 10 g of poly(isobutylene-alt-maleic anhydride) (PIBMA) (Avg. Mw=6000 g/mol) in 60 ml of DMF, 7.96 g of 3-Aminopropyldimethylamine (relative to the monomer weight) is added and stirred at 120° C. for 48 h in a screw-top pressure tube. The reaction mixture is cooled, precipitated with 200 ml of distilled water and is centrifuged at 10,000 rpm for 15 min. The polymer is dried at 45° C. for 24 h under vacuum to give a pale yellow solid (yield: 100%): FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$H-NMR (400 MHz, CDCl$_3$): δ/ppm 0.8-1.2 (br CH$_2$C(C$_3$)$_2$, 6H), 1.7 (br CH$_2$C(CH$_3$)$_2$, 2H), 2.0 (br NCH$_2$CH$_2$CH$_2$N(CH$_3$)$_2$, 2H), 2.2-2.5 (br NCH$_2$CH$_2$CH$_2$N(CH$_3$)$_2$, 8H), 2.7-3.1 (br, CHCH, 2H), 3.6 (br NCH$_2$CH$_2$CH$_2$N(CH$_3$)$_2$, 2H); $^{13}$C-NMR (100 MHz, CDCl$_3$): 179.9, 179.7, 179.4, 177.4, 177.3, 177.2, 55.5, 45.9, 45.5, 44.1, 40.8, 40.6, 40.2, 40.0, 37.4, 26.2, 25.5, 24.8, 24.7, and 24.6.

Example: 2

Synthesis of Protonated PIBMI Derivative, QPro_PIBMI 0.5 g of PIBMI is dissolved in 10 ml of 2 M HBr solution and stirred at room temperature for 12 h. The product is obtained by dialysing against DI water (benzoylated dialysis tubing with NMWCO of 2 KDa) at 4° C. followed by freeze-drying (yield:100%): FT-IR: 3300 $cm^{-1}$ (N—H str.), 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$H NMR (400 MHz, D$_2$O): δ/ppm 0.8-1.2 (br CH$_2$C(CH$_3$)$_2$, 6H), 1.7 (br CH$_2$C(CH$_3$)$_2$, 2H), 2.0 (br NCH$_2$CH$_2$CH$_2$N(CH$_3$)$_2$, 2H), 2.8-2.9 (br NCH$_2$CH$_2$CH$_2$N (CH$_3$)$_2$, 8H), 2.7-3.1 (br, CHCH, 2H), 3.6 (br NCH$_2$CH$_2$CH$_2$N(CH$_3$)$_2$, 2H).

Example 3

Poly(isobutylene-alt-N—(N',N'-dimethyl N'-n-alkyl/OEG aminopropyl)-maleimide)-QAlk_PIBMI/QOEG_PIBMI To a solution of 0.5 g of PIBMI in 20 ml of dry DMF/CHCl$_3$, 1.04 g of 1-bromoalkane (1-bromo ethane, 1-bromo butane, 1-bromo pentane, 1-bromo hexane, 1-bromo heptane, 1-bromo octane or 1-bromo decane) or 1.15 g of 1-bromo-2-(2-methoxyethoxy)ethane (relative to the monomer weight) is added and stirred at 75° C. for 96 h in a screw top pressure tube. The solution is cooled, precipitated with 40 ml of n-hexane/diethylether and filtered. The white solid is washed with n-hexane (4×40 ml) and dried at 40° C. for 12 h under vacuum (yield: 100%).

QDec_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$CH$_2$CH$_2$CH$_2$CH$_2$CH$_2$CH$_2$, 16H) 1.7 (br CH$_2$C (CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N(CH$_3$)$_2$, 2H).

QOct_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$CH$_2$CH$_2$CH$_2$CH$_2$, 12H) 1.7 (br CH$_2$C(CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N(CH$_3$)$_2$, 2H).

QHep_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$CH$_2$CH$_2$, CH$_2$, 10H) 1.7 (br CH$_2$C(CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N(CH$_3$)$_2$, 2H).

QHex_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$CH$_2$CH$_2$, 8H) 1.7 (br CH$_2$C(CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N(CH$_3$)$_2$, 2H).

QPen_PIBMI: -FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$CH$_2$, 6H) 1.7 (br CH$_2$C(CH$_3$)$_2$, 2H), 2.0 (br NCH$_2$CH$_2$CH$_2$N (CH$_3$)$_2$, 2H), 2.7-3.1 (br CHCH, 2H), 3.1-3.3 (br NCH$_2$CH$_2$CH$_2$NCH$_2$(CH$_2$10), 3.6 (br NCH$_2$CH$_2$CH$_2$N (CH$_3$)$_2$, 2H).

QBut_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.3-1.5 (br CH$_2$CH$_2$, 4H) 1.7 (br CH$_2$C(CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N (CH$_3$)$_2$, 2H).

QEth_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.85-0.9 (br terminal —CH$_3$, 3H), 0.95-1.2 (br CH$_2$C(CH$_3$)$_2$, 6H), 1.7 (br CH$_2$C(CH$_3$)$_2$, 2H), 2.0 (br NCH$_2$CH$_2$CH$_2$N(CH$_3$)$_2$, 2H), 2.7-3.1 (br CHCH, 2H), 3.1-3.3 (br NCH$_2$CH$_2$CH$_2$NCH$_2$(CH$_3$)$_2$, 10H), 3.6 (br NCH$_2$CH$_2$CH$_2$N(CH$_3$)$_2$, 2H).

QOEG_PIBMI: FT-IR: 2950-2850 (C—H str.), 1767 $cm^{-1}$ (C=O asym. str.), 1696 $cm^{-1}$ (C=O sym. str.) 1470-1410 $cm^{-1}$ (C—C str.), 1290-1110 (C—O str.); $^1$HNMR (400 MHz, D$_2$O): δ/ppm 0.95-1.2 (br CH$_2$C(CH$_3$)$_2$, 6H), 1.7 (br CH$_2$C(CH$_3$)$_2$, 2H), 2.0 (br NCH$_2$CH$_2$N(CH$_3$)$_2$, 2H), 2.7-3.1 (br CHCH, 2H), 3.1-3.2 (br NCH$_2$(CH$_3$)$_2$, 6H), 3.45

(s, terminal —CH$_3$), 3.55-3.8 (br, NCH$_2$CH$_2$CH$_2$NCH$_2$(CH$_3$)$_2$ and OCH$_2$CH$_2$O, 10H), 4.0 (br OCH2CH$_2$N(CH$_3$)$_2$, 2H).

Example: 4

The synthesis of the ester and amide based alkylating agents is represented in FIG. 5.

Synthesis of N-propyl-1-bromoethanamide

Propylamine (7 g, 118 mmol) is dissolved in dichloromethane (55 mL). Potassium carbonate, K$_2$CO$_3$ (24.55 g, 178 mmol) is dissolved in 60 ml of distilled water and the solution is added to the organic solution. The resulting two phase solution is cooled to 5° C. A solution of bromoacetyl bromide (35.85 g, 178 mmol) in dichloromethane (55 mL) is carefully added drop wise to the cooled solution while maintaining the temperature at 5° C. for about 30 min. Then the reaction mixture is stirred at room temperature for 12 h. The aqueous solution is separated and washed with dichloromethane (2×25 mL). The organic solution is washed with water (2×50 mL) and passed over the anhydrous Na$_2$SO$_4$ and concentrated to yield an oily liquid quantitatively: FT-IR: 3250 cm$^{-1}$ (amide N—H str.), 2950-2850 (C—H str.), 1680 cm$^{-1}$ (Amide I, C=O str.), 1560 cm$^{-1}$ (Amide II, N—H ben.), 1470-1410 cm$^{-1}$ (C—C str.), 1290-1110 (C—O str.); $^1$HNMR (400 MHz, CDCl$_3$): δ/ppm 0.878 (t, terminal —CH$_3$, 3H), 1.543 (m, —CH$_2$CH$_3$—, 2H), 3.278 (t, —CONHCH$_2$—, 2H), 3.881 (s, —COCH$_2$Br, 2H), 6.475 (br s, amide —NHCO, 1H)); $^{13}$C NMR (100 MHz, CDCl$_3$): δ14.195, 22.768, 26.904, 29.324, 29.423, 29.588, 29.646, 29.708, 31.995, 40.403, 165.589.

Synthesis of Propyl-1-bromoethanoate

1-Propanol (7 g, 116.5 mmol) is dissolved in dichloromethane (55 mL). Potassium carbonate, K$_2$CO$_3$ (19.32 g, 140 mmol) is dissolved in 60 ml of distilled water and the solution is added to the organic solution. The resulting two phase solution is cooled to 5° C. A solution of bromoacetyl bromide (28.21 g, 140 mmol) in dichloromethane (55 mL) is carefully added drop wise to the cooled solution while maintaining the temperature at 5° C. for about 30 min. Then the reaction mixture is stirred at room temperature for 12 h. The aqueous solution is separated and washed with dichloromethane (2×25 mL). The organic solution is washed with water (2×50 mL) and passed over the anhydrous Na$_2$SO$_4$ and concentrated to yield an oily liquid quantitatively: FT-IR: 2950-2850 (C—H str.), 1735 cm$^{-1}$ (C=O str.), 1470-1410 cm$^{-1}$ (C—C str.), 1290-1110 (C—O str.); $^1$H NMR (400 MHz, CDCl$_3$): δ/ppm 0.85 (t, terminal —CH$_3$, 3H), 1.57 (m, —CH$_2$CH$_3$—, 2H), 4.0 (t, —COOCH$_2$—, 2H), 3.7 (s, —COCH$_2$Br, 2H); $^{13}$C NMR (100 MHz, CDCl$_3$): δ 14.195, 22.768, 26.904, 29.324, 29.423, 29.588, 29.646, 29.708, 31.995, 40.403, 171.19.

Example 5

Poly(isobutylene-alt-N—(N',N'-dimethyl N'-(propyl ethanoate/N''-propyl ethanamide)aminopropyl)-maleimide)-QEst_PIBMI/QAmi_PIBMI To a solution of 0.5 g of PIBMI in 20 ml of dry DMF/dry CHCl$_3$, 0.76 g of propyl-1-bromoethanoate/N-propyl-1-bromoethanamide (relative to the monomer weight) is added and stirred at 65° C.-75° C. for 96 h in a screw top pressure tube. The solution is cooled, precipitated with 40 ml of diethylether and filtered. The white solid is washed with diethylether (4×40 ml) and dried at 40° C. for 4 h under vacuum (yield: 100%).

QEst_PIBMI: FT-IR: 2950-2850 (C—H str.), 1767 cm$^{-1}$ (imide C=O asym. str.), 1696 cm$^{-1}$ (imide C=O sym. str.), 1735 cm$^{-1}$ (ester C=O str.) 1470-1410 cm$^{-1}$ (C—C str.), 1290-1110 (C—O str.); $^1$H NMR (400 MHz, D$_2$O): δ/ppm 0.85 (br, terminal —CH$_3$, 3H), 0.95-1.2 (br, CH$_2$C(CH$_3$)$_2$, 6H), 1.57 (br, —COOCH$_2$CH$_2$CH$_3$, 2H), 1.7 (br, CH$_2$C(CH$_3$)$_2$, 2H), 2.0 (br, NCH$_2$CH$_2$CH$_2$N(CH$_3$)$_2$, 2H), 2.7-3.1 (br, CHCH, 2H), 3.1-3.3 (br, NCH$_2$CH$_2$CH$_2$N(CH$_3$)$_2$, 8H), 3.6 (br, NCH$_2$CH$_2$CH$_2$N(CH$_3$)$_2$, 2H), 3.7 (br, —N(CH$_3$)$_2$COCH$_2$, 2H) 4.0 (br, —COOCH$_2$—, 2H).

QAmi_PIBMI: FT-IR: 3250 cm$^{-1}$ (amide N—H str.), 2950-2850 (C—H str.), 1767 cm$^{-1}$ (imide C=O asym. str.), 1696 cm$^{-1}$ (imide C=O sym. str.) 1680 cm$^{-1}$ (amide I, C=O str.), 1560 cm$^{-1}$ (Amide II, N—H ben.), 1470-1410 cm$^{-1}$ (C—C str.), 1290-1110 (C—O str.); $^1$H NMR (400 MHz, D$_2$O): δ/ppm 0.878 (br, terminal —CH$_3$, 3H), 0.95-1.2 (br, CH$_2$C(CH$_3$)$_2$, 6H), 1.543 (br, —CONHCH$_2$CH$_2$CH$_3$—, 2H), 1.7 (br, CH$_2$C(CH$_3$)$_2$, 2H), 2.0 (br, NCH$_2$CH$_2$CH$_2$N(CH$_3$)$_2$, 2H), 2.7-3.1 (br, CHCH, 2H), 3.1-3.3 (br, NCH$_2$CH$_2$CH$_2$N(CH$_3$)$_2$, 8H), 3.5 (br, —CONHCH$_2$—, 2H), 3.6 (br, NCH$_2$CH$_2$CH$_2$N(CH$_3$)$_2$, 2H), 3.8 (br, —N(CH$_3$)$_2$COCH$_2$, 2H).

Example 6

All the polymeric derivatives are characterized using FT-IR, $^1$H NMR and $^{13}$C NMR. Degree of quaternization of the polymeric derivatives is calculated using $^1$H NMR analysis (Table 1 and FIG. 6). All the polymers have similar degree of quaternization (93-98%) which makes it easy for a very good comparison between their amphiphilicity and selectivity (Table 1).

Degree of quaternization of the polymeric derivatives is calculated using $^1$H NMR analysis as (FIG. 6):
(a) for 1.7 (br CH$_2$C(CH$_3$)$_2$, 2H) and (b) for 2.2-2.5 (br, NCH$_2$CH$_2$CH$_2$N(CH$_3$)$_2$, 8H)

Degree of quaternization $(d)=(1-e)\times 100\%$

Wherein e={([CH$_2$N(CH$_3$)$_2$]/8)/([CH$_2$C(CH$_3$)$_2$]/2)}
e={(m/8)/(n/2)}, m=[CH$_2$N(CH$_3$)$_2$] and n=[CH$_2$C(CH$_3$)$_2$]

For e.g. QHex_PIBMI, Degree of quaternization $(d)=1-\{(0.32/8)/(2.0/2)\}\times 100\%=96\%$ wherein, [CH$_2$C(CH$_3$)$_2$] and [CH$_2$N(CH$_3$)$_2$] are the integrals of the hydrogens (a and b respectively, shown in FIG. 6) those are bold and italicized.

The molecular weight ($M_n$) of the final derivatives is calculated based on the molecular weight of the precursor (Mw~6000 Da, monomer weight is 154 g/mol and L~39) and the degree of quaternization and is given in Table 1.)

TABLE 1

Degree of Quaternization of the Polymeric Derivatives

| Polymer | Degree of Quaternization $^1$H NMR/% | $M_n$ (10$^4$ g/mol)$^a$ |
|---|---|---|
| QEth_PIBMI | 95 | 1.63 |
| QBut_PIBMI | 95 | 1.73 |
| QPen_PIBMI | 96 | 1.79 |
| QHex_PIBMI | 96 | 1.85 |
| QHep_PIBMI | 94 | 1.88 |
| QOct_PIBMI | 93 | 1.92 |

TABLE 1-continued

Degree of Quaternization of the Polymeric Derivatives

| Polymer | Degree of Quaternization $^1$H NMR/% | $M_n$ ($10^4$ g/mol)$^a$ |
|---|---|---|
| QDec_PIBMI | 94 | 2.0 |
| QAmi_PIBMI | 98 | 1.92 |
| QEst_PIBMI | 96 | 1.90 |
| QOEG_PIBMI | 97 | 1.92 |

$^a$Calculated from molecular weight of precursor copolymers and degree of quaternization.

Example 7

Chemical Degradation of QEst_PIBMI, QPen_PIBMI and poly(isobutylene-alt-maleic anhydride) (FIG. 7)

The ester hydrolysis of the QEst_PIBMI is done using 8 M HCl at 50° C. for 72 h to give the zwitterionic derivative QZwi_PIBMI. Treatment of either the QEst_PIBMI or QZwi_PIBMI with 1 M NaOH at 50° C. for 24 h degrades the succinimide ring yielding the corresponding open ring by-product with net anionic charge. Both the by-products are obtained after dialyzing against DI water at room temperature using a dialysis membrane (Mol. wt. cut off=10 KDa) followed by freeze-drying. Similarly, the succinimide ring opening of QPen_PIBMI was achieved after heating in 1 M NaOH at 50° C. for 24 h. All these by-products were obtained after dialyzing against DI water at room temperature using a dialysis membrane (Mol. wt. cut off=10 KDa) followed by freeze-drying. Poly(isobutylene-alt-maleic acid) is synthesized by treatment of poly(isobutylene-alt-maleic anhydride) with 1 M NaOH at 80° C. for 24 h followed by dialysis against DI water (benzoylated dialysis tubing with NMWCO of 2 KDa) at 4° C. and freeze-drying.

QZwi_PIBMI: FT-IR: 2950-2850 (C—H str.), 1767 cm$^{-1}$ (imide C=O asym. str.), 1696 cm$^{-1}$ (imide C=O sym. str.) 1634 cm$^{-1}$ (carboxylate C=O str.), (1470-1410 cm$^{-1}$ (C—C str.), 1290-1110 (C—O str.); $^1$H NMR (400 MHz, D$_2$O): δ/ppm 0.95-1.2 (br, CH$_2$C(CH$_3$)$_2$, 6H), 1.7 (br, CH$_2$C(CH$_3$)$_2$, 2H), 2.0 (br, NCH$_2$CH$_2$CH$_2$N(CH$_3$)$_2$, 2H), 2.7-3.1 (br, CHCH, 2H), 3.1-3.3 (br, NCH$_2$CH$_2$CH$_2$N(CH$_3$)$_2$, 8H), 3.6 (br, NCH$_2$CH$_2$CH$_2$N(CH$_3$)$_2$, 2H), 4.1-4.3 (br, —N(CH$_3$)$_2$COCH$_2$, 2H):

QOpr_PIBMI: FT-IR: 3250 cm$^{-1}$ (amide N—H str.), 2950-2850 (C—H str.), 1680 cm$^{-1}$ (amide I, C=O str.), 1634 cm$^{-1}$ (zwitterionic carboxylate C=O str.), 1580 cm$^{-1}$ (sodium carboxylate C=O str), 1560 cm$^{-1}$ (Amide II, N—H ben.), (1470-1410 cm$^{-1}$ (C—C str.), 1290-1110 (C—O str.).

QOPen_PIBMI: FT-IR: 3250 cm$^{-1}$ (amide N—H str.), 2950-2850 (C—H str.), 1680 cm$^{-1}$ (amide I, C=O str.), 1580 cm$^{-1}$ (sodium carboxylate C=O str), 1560 cm$^{-1}$ (Amide II, N—H ben.), (1470-1410 cm$^{-1}$ (C—C str.), 1290-1110 (C—O str.).

PIBMA: FT-IR: 2950-2850 (C—H str.), 1720 cm$^{-1}$ (C=O str.), (1470-1410 cm$^{-1}$ (C—C str.), 1290-1110 (C—O str.).

Example 8

The method of forming the nanoparticles of the compounds can be by organizing their self-assembly in aqueous solution at concentration above their critical aggregation concentrations (CAC, see below).

Critical Aggregation Concentration (FIG. 8)

The aggregation properties of the polymers in aqueous solution are investigated by static light scattering measurements on a PerkinElmer LS-55 Luminescence Spectrometer. Q-PIBMI derivatives at an initial concentration of 10 mg mL$^{-1}$ are successively diluted in 2 ml of PBS (pH=7.4)/MH broth at room temperature, and light scattering is evaluated by measuring the reflected light at an angle of 90°, holding both the excitation and the emission at 400 nm. An excitation slit width of 10 nm and an emission slit width of 2.5 nm are used and kept invariable throughout the experiment. The static light scattering signal is proportional to the number of aggregated molecules and the size of the aggregate. To describe the dependence of scattered signal on polymer concentration, the intensity of scattered light is plotted against total polymer concentrations using Origin Pro 8.0 software. The critical aggregation (intermolecular) concentration (CAC) is determined from the intersection of the two lines formed by linear regression calculated for the concentrations that show low scattered intensity and those that show high scattered intensity. Similar experiments are performed with water (Table 2) and the media (Table 3) used to grow the bacteria and obtained the CAC values accordingly.

For example derivatives QHex_PIBMI, QAmi_PIBMI and QEst_PIBMI have CACs of 0.6, 1.3 and 1.9 mg mL$^{-1}$ in PBS (pH=7.4) respectively (FIG. 8B-D). In MH broth, these derivatives have significantly lower CAC values (CAC=2.2 μg mL$^{-1}$ for QHex_PIBMI) due to the presence of salts and nutrients (FIG. 8A). For example, above its CAC, QHex_PIBMI shows an average diameter (hydrodynamic) of 220 nm and a zeta potential of 38±7 mV, when studied using dynamic light scattering (DLS, Table 2). As expected, the CAC of the polymeric derivatives is found to increase as the nature of the alkylating agent was varied from hydrophobic to amphiphilichydrophilic (Table 2 and 3). QHex_PIBMI with highly hydrophobic C6 long chain displays a lower CAC in PBS and media compared to QAmi_PIBMI and QEst_PIBMI containing amphiphilic alkylating agents (Table 2 and 3).

Example 9

Size (Hydrodynamic Diameter) and Zeta Potential

Nanoparticle size (hydrodynamic diameter) and zeta potential of the quaternized PIBMI derivatives are measured in water (Table 2) and media (Table 3) by phase analysis light scattering and dynamic light scattering respectively using Brookhaven ZetaPALS Zeta Potential and Particle Size Analyzer. The measurement of particle size is done at a scattering angle of 90°. For all the derivatives, both the measurements are conducted at concentrations above their respective CAC values.

TABLE 2

Aggregation properties of Quaternized PIBMI Derivatives in Water

| Polymer | CAC (mg/ml) in DI water $^a$ | Size* (nm) | Zeta potential* (mV) |
|---|---|---|---|
| QHex_PIBMI | 0.6 | 482 ± 64 | 34 ± 2 |
| QPen_PIBMI | 3.0 | 532 ± 37 | 30 ± 2 |
| QAmi_PIBMI | 1.26 | 413 ± 19 | 41 ± 2 |
| QEst_PIBMI | 1.91 | 431 ± 48 | 35 ± 3 |
| QOEG_PIBMI | 0.67 | 358 ± 7 | 32 ± 6 |

$^a$ CAC is determined using static light scattering studies
*Size and zeta potential are obtained from dynamic light scattering studies

TABLE 3

Aggregation properties of Quaternized
PIBMI Derivatives in Peptone Media

| Compound | CAC[a] (μg/mL) | Effective Diameter[b] (nm) |
|---|---|---|
| QHex_PIBMI | 2.2 | 226 |
| QPen_PIBMI | 6.9 | 189 |
| QAmi_PIBMI | 4.65 | 364 |
| QEst_PIBMI | 8.95 | 328 |
| QOEG_PIBMI | 15.8 | 475 |

[a]CAC is determined by static light scattering(SLS) in Peptone media.
[b]Size determination is done by dynamic light scattering (DLS) in Peptone media at 20 μg/mL.

Example: 10

Nanoparticle Characterization by Scanning Electron Microscopy (SEM) (FIG. 9)

SEM images of the cationic polymer nanoparticles are obtained using Quanta 3D FEG (FEI) field emission scanning electron microscope operating at an accelerating voltage of 4.0-6.0 keV. To prepare the SEM sample, 5 μl of aqueous solution of polymer (5 mg mL$^{-1}$) is placed on the silicon wafer, and air dried at room temperature.

QHex_PIBMI at concentration above its CAC forms spherical aggregates with size distribution of 50-130 nm. QEst_PIBMI at a concentration above its CAC shows different non-spherical morphology and larger size distribution of 200-500 nm compared to QHex_PIBMI (FIG. 9).

Example: 11

Bio-Assays of the Polymers

Microorganisms and Culture Conditions

The antibacterial activity of the compounds is done against both Gram-negative (E. coli; MTCC 443) and Gram-positive (S. aureus; MTCC 737) bacteria. E. coli is cultured in Luria Bertani broth (10 g of tryptone, 5 g of yeast extract, and 10 g of NaCl in 1000 mL of sterile distilled water (pH −7) while S. aureus, P. aeruginosa and MRSA are grown in Yeast-dextrose broth (1 g of beef extract, 2 g of yeast extract, 5 g of peptone and 5 g of NaCl in 1000 mL of sterile distilled water). For E. faecium and VRE, Brain Heart Infusion broth (BHI) is used. K. pneumoniae is grown in nutrient media (3 g of beef extract and 5 g of peptone in 1000 mL of sterile distilled water). For solid media 5% agar is used along with above mentioned composition. The bacterial samples are freeze dried and stored at −80° C. 5 μl of these stocks are added to 3 mL of the nutrient broth and the culture is grown for 6 h at 37° C. prior to the experiments.

Antibacterial Activity (FIG. 10 and Table 4-5):

Antibacterial activity is determined with the slight modifications of standardized protocols. Water-soluble Q-PIBMI derivatives are assayed in a modified micro-dilution broth format. Stock solutions are made by serially diluting the compounds using autoclaved Millipore water. Bacteria, to be tested, grown for 6 h in the suitable media containing ~10$^9$ cfu/mL (determined by spread plating method), which is then diluted to 10$^5$ cfu/mL using nutrient media. 50 μL of serially diluted compound is added to a 96 well plate containing 150 μL bacterial solutions. Two controls are made; one containing 150 μL of media and 50 μL of compound and the other containing 200 μL of bacterial solution. The plate is then incubated at 37° C. for a period of 24 h and MIC data is recorded by measuring the O.D. value at 600 nm using a Tecan InfinitePro series M200 Microplate Reader. MIC value is determined by taking the average of triplicate O.D. values for each concentration and plotting it against concentration using Origin Pro 8.0 software. The data is then subjected to sigmoidal fitting. From the curve the MIC value is determined, as the point in the curve where the O.D. is similar to that of control having no bacteria. The MIC values and errors are reported as averages and standard errors of mean of three independent experiments respectively. MIC curves for each polymer are representative data from the three independent experiments and each experiment was performed in triplicates (FIG. 10 and Tables 4-5). For determination of Minimum bactericidal concentration (MBC), 50 μl of the suspension is taken and plated on solid media agar plates for CFU count, using the spread plate method. CFUs are counted after 24 h incubation at 37° C. MBC is measured as the concentration at which no bacterial colonies are present (Table 6).

TABLE 4

Antibacterial activity and selectivity
of Quaternized PIBMI Derivatives

| | MIC(μg mL$^{-1}$) | | HC$_{50}$ | Selectivity* | |
|---|---|---|---|---|---|
| Polymer | E. coli | S. aureus | (μg mL$^{-1}$) | E. coli | S. aureus |
| QPro_PIBMI | 105 | 91 | >1000 | 9.5 | 11 |
| QEth_PIBMI | >1000 | >1000 | >1000 | <1 | <1 |
| QBut_PIBMI | 45 | 67 | >1000 | 22 | 15 |
| QHep_PIBMI | 13 | 13 | 12 | 0.9 | 0.9 |
| QOct_PIBMI | 16 | 16 | 8.9 | 0.5 | 0.5 |
| QDec_PIBMI | 118 | 57 | 4.2 | 0.03 | 0.07 |

*Selectivity (HC$_{50}$/MIC)

TABLE 5

Antibacterial activity and selectivity of Quaternized PIBMI Derivatives

| | MIC (μg mL$^{-1}$) | | | | | | | HC$_{50}$ |
|---|---|---|---|---|---|---|---|---|
| | Gram-negative | | | Gram-positive | | | | |
| Polymer | E. coli | K. pneumoniae | P. aeruginosa | S. aureus | E. faecium | MRSA[a] | VRE[b] | (μg mL$^{-1}$) |
| QHex_PIBMI | 7 (4.3) | 36 (0.8) | 62 (0.5) | 20 (1.5) | 4 (7.5) | 113 (0.3) | 4 (7.5) | 30 |
| QPen_PIBMI | 14 (24.5) | 57 (6) | 94 (4) | 3 (114) | 8 (43) | 104 (3.5) | 4 (86) | 343 |
| QAmi_PIBMI | 2.2 (>45) | 59 (>17) | 101 (>10) | 11 (>91) | 15 (>67) | 224 (>4.5) | 6 (>166) | >1000 |
| QEst_PIBMI | 65 (>15.4) | 46 (>22) | 208 (>4.8) | 11 (>91) | 510 (>2) | >1000 | 123 (>8) | >1000 |

TABLE 5-continued

Antibacterial activity and selectivity of Quaternized PIBMI Derivatives

| | MIC (µg mL$^{-1}$) | | | | | | | HC$_{50}$ |
|---|---|---|---|---|---|---|---|---|
| | Gram-negative | | | Gram-positive | | | | |
| Polymer | E. coli | K. pneumoniae | P. aeruginosa | S. aureus | E. faecium | MRSA[a] | VRE[b] | (µg mL$^{-1}$) |
| QOEG_PIBMI | >1000 | 150 (>6.6) | >1000 | 20 (>50) | >1000 | >1000 | >1000 | >1000 |
| Vamcomycin | ND | ND | ND | ND | ND | ND | >156 | ND |

[a]Methicillin resistant *Staphylococcus aureus*,
[b]Vancomycin resistant *Enterococcus faecium*,
Selectivity (HC$_{50}$/MIC) is given in parenthesis.
ND—not determined.

Example: 12

Bactericidal Time-Kill Kinetics

The bactericidal activity of the derivatives is assessed by its kinetics. Briefly, *S. aureus* is grown in yeast-dextrose broth at 37° C. for 6 h. Test compound QPen_PIBMI having final concentration of 6×MIC, 12×MIC, 18×MIC, 24×MIC and 30×MIC is inoculated with the aliquots of *S. aureus* resuspended in fresh media at approximately 1.8×10$^5$ CFU mL$^{-1}$. After 8 and 24 h), 20 µL aliquots are serially diluted 10 fold in 0.9% saline, plated on sterile yeast-dextrose agar plates and incubated at 37° C. overnight. The viable colonies are counted the next day and represented as CFU mL$^{-1}$ (Table 6). Test compound, QAmi_PIBMI, having the final concentrations of 1×MIC, 6×MIC and 12×MIC is inoculated with the aliquots of *S. aureus* resuspended in fresh media at approximately 1.8×10$^5$ CFU mL$^{-1}$. After specified time intervals (0, 1, 2, 3, 6, and 24 h), 20 µL aliquots are serially diluted 10 fold in 0.9% saline, plated on sterile yeast-dextrose agar plates and incubated at 37° C. overnight. The viable colonies are counted the next day and represented as log$_{10}$ (CFU mL$^{-1}$) (FIG. 11).

The minimum bactericidal concentration (MBC) of the derivatives after 24 h treatment is measured and the derivatives are found to be bactericidal at low concentrations (Table 7). The most effective derivative, QPen_PIBMI is bactericidal at low concentration of 4 µg mL$^{-1}$ against *S. aureus* whereas QHex_PIBMI is bactericidal at 16 µg mL$^{-1}$ against *E. coli*. Time-based bactericidal kinetics of QPen_PIBMI against *S. aureus* is performed, wherein QPen_PIBMI, after 8 and 24 hours of incubation with 72 µg mL$^{-1}$ shows no colonies whereas the control has nearly 10$^{11}$ and 10$^{17}$ CFU/mL respectively (Table 6). Additionally, to prove the bactericidal activity of the derivatives, the time-kill curves are also generated for QAmi_PIBMI against *S. aureus* as the model bacterium. QAmi_PIBMI shows a rapid 5 log$_{10}$ of reduction of bacteria within 2 h and 1 h at a concentration of about 6 and about 12 times the MIC respectively whereas at MIC it rather shows bacteriostatic activity (FIG. 11).

TABLE 7

Bactericidal Action of Quaternized PIBMI Derivatives

| | MBC(µg/mL) | |
|---|---|---|
| Polymer | E. coli | S. aureus |
| QHex_PIBMI | 16 | 31 |
| QPen_PIBMI | 31 | 4 |
| QAmi_PIBMI | 31 | 16 |
| QEst_PIBMI | 125 | 16 |
| QOEG_PIBMI | >1000 | 62 |

Example: 13

Antibacterial Efficacy in Human Plasma

The antibacterial activity of the derivatives is performed in presence of 50% of plasma to assess its susceptibility to plasma proteases. 250 µL of the compound is added to 250 µL of human plasma (centrifuged from whole blood and collected the blood minus cell fraction) and preincubated at 37° C. for 0, 3 and 6 h (final concentration of human plasma is 50% (vol/vol)). After incubation, the compound is diluted two-fold in 0.9% saline. The antibacterial assay is performed against *S. aureus* and MIC is determined as described above. Also, a similar MIC experiment against *S. aureus* is performed in the absence of the plasma as control (Table 8).

For the first time in the field of polymeric mimics of AMPs, to assess the compound's stability, MIC experiment of QPen_PIBMI and QAmi-PIBMI is performed against *S. aureus* as a model bacterium in 50% of human plasma. The MIC values are given in Table 8.

TABLE 6

Bactericidal kinetics of QPen_PIBMI against *S. aureus*

| Time | 6 × MIC | 12 × MIC | 18 × MIC | 24 × MIC | 30 × MIC | Control |
|---|---|---|---|---|---|---|
| 8 hr | 1.8 × 10$^{11}$ CFU/ml | 9.4 × 10$^{10}$ CFU/ml | 7.1 × 10$^8$ CFU/ml | 0 | 0 | 1.8 × 10$^{11}$ CFU/ml |
| 24 hr | 1.0 × 10$^{13}$ CFU/ml | 1.1 × 10$^{10}$ CFU/ml | 5.7 × 10$^5$ CFU/ml | 0 | 0 | 2.5 × 10$^{17}$ CFU/ml |

TABLE 8

Effect of human plasma on the antibacterial efficacy of the quaternized PIBMI derivatives

| Polymer | MIC (µg mL$^{-1}$) in 50% of human plasma + 50% of media | | | MIC (µg mL$^{-1}$) in 100% of media |
|---|---|---|---|---|
| | 0 h$^a$ | 3 h$^a$ | 6 h$^a$ | |
| QPen_PIBMI | 10 | 13 | 26 | 3 |
| QAmi_PIBMI | 12 | 20 | 48 | 11 |

$^a$Preincubation in 50% of human plasma (h)

Example 14

Hemolytic Activity

The hemolytic activity is determined against human erythrocytes according to Antibacterial Peptides Protocols with slight modifications. Erythrocytes are isolated from freshly drawn, heparanized human blood and resuspended to 5% v/v in PBS (pH 7.4). In a 96-well microtiter plate, 150 µL of erythrocyte suspension is added followed by 50 µL of serially diluted compound to give a final solution of 3.75% v/v erythrocytes. PBS buffer is added instead of polymer solution as negative hemolysis control and Triton X-100 (1% v/v) is used as positive hemolysis control. The plate is incubated for 1 h at 37° C. The plate is then centrifuged at 3,500 rpm for 5 min, 100 µL of the supernatant from each well is transferred to a fresh micro titer plate, and absorbance at 414 nm is measured. Percentage of hemolysis is determined as $(A-A_0)/(A_{total}-A_0) \times 100$, where A is the absorbance of the test well, $A_0$ the absorbance of the negative controls, and $A_{total}$ the absorbance of 100% hemolysis wells, all at 540 nm. Hemolysis is plotted as a function of polymer concentration and the $HC_{50}$ is defined as the polymer concentration, which causes 50% hemolysis relative to the positive control. In some cases, hemolysis does not reach 50% up to the highest polymer concentration tested (1 µg mL$^{-1}$ or 40 µg mL$^{-1}$) and the $HC_{50}$ is not determined. The $HC_{50}$ values and errors are reported as averages and standard errors of mean of three independent experiments, respectively (FIG. 10 and Table 4-5). Hemolysis curves for each polymer are representative data from two independent experiments and each experiment is performed in triplicates.

All the three polymeric degradation by-products are shown to be non-hemolytic up to 40000 µg mL$^{-1}$ (FIG. 12).

Example 15

In-Vivo Systemic and Sub-Chronic Toxicity Studies

All the experiments involving animals are performed according to the protocols approved by the JNCASR's Institutional Animal Ethics Committee (IAEC, registered with the CPCSEA (Reg. No. 201/CPCSEA), Government of India). Parameters analyzed in subchronic toxicity studies are chosen as per the FDA guidelines of Subchronic Toxicity Study in Rodents. Female Balb/c mice (6-8 weeks, 18-22 g) are used for both systemic and subchronic toxicity studies. 200 µL of the solution in sterilized PBS (pH=7.4) is injected into 5-6 mice per group via tail vein at different doses [i.e. Two sets of five mice each are tested for doses of 0, 1.1, 3.5, 11 and 35 mg kg$^{-1}$ of QPen_PIBMI and QAmi_PIBMI, five mice are tested for doses of 0, 2, 10, 20 and 40 mg kg$^{-1}$ of QEst_PIBMI] and all the mice are monitored for 14 days post-treatment. For the toxicity studies of the polymeric by-products, QZwi_PIBMI and QOpr_PIBMI, 5 mice for one compound were injected with 400 mg kg$^{-1}$, the highest tested dose.

Experiments performed to assess the in-vivo systemic toxicity of QPen_PIBMI, QAmi_PIBMI and QEst_PIBMI after single-dose intravenous (i.v.) administration to mice (n=5-6) reveal no mortality and no signs of adverse effects at least up to 3.5, 11 and 20 mg kg$^{-1}$ body weight respectively and their $LD_{50}$ values are found to be 9, 20 and 37 mg kg$^{-1}$ respectively (Table 9).

The in-vivo systemic toxicity of the polymeric by-products QZwi_PIBMI and QOpr_PIBMI obtained after chemical degradation from QAmi_PIBMI/QEst_PIBMI is investigated. It is found that they do not induce any mortality in mice up to 400 mg kg$^{-1}$, which is the highest tested dose.

TABLE 9

In-vivo toxicity studies of quaternized PIBMI derivatives in mice models

| Polymer | $LD_{50}$ (mg kg$^{-1}$) |
|---|---|
| QPen_PIBMI | 9 |
| QAmi_PIBMI | 20 |
| QEst_PIBMI | 37 |

For evaluating the subchronic toxicity (clinical biochemistry parameters), six groups of 10 mice each are given intravenous (i.v.) injection of QPen_PIBMI (20 mice), QAmi_PIBMI (20 mice) and QEst_PIBMI (20 mice) at a dosage of 2 mg kg$^{-1}$ in 200 µL of sterilized PBS (pH=7.4) and 10 mice are used for the control group. After 48 h, blood is collected from 30 mice and analyzed for different parameters like alkaline phosphatase (ALP), creatinine, blood urea nitrogen, and electrolytes like sodium, potassium ions and chloride. Further, after 14 days, blood is collected from the remaining 30 mice and analyzed for the above mentioned parameters. Similarly, all the above parameters are analyzed for the control group as well (Tables 10 and 11).

Also, the subchronic toxicity to major organs in the body of the mice is investigated by evaluating the clinical biochemistry parameters in the blood of the mice after a single-dose i.v. administration of QPen_PIBMI, QAmi_PIBMI and QEst_PIBMI (at a dosage of 2 mg kg$^{-1}$, a concentration well above the MICs of the derivatives). None of the three derivatives induce adverse toxicity to major organs like liver and kidney and does not interfere with the balance of electrolytes in the blood of mice 48 h post treatment compared to vehicle control and laboratory parameters (Table 10). These parameters remain almost unchanged even after 14 days post-treatment (Table 11). All the parameters tested related to the function of major organs like liver, kidney and electrolytes in the blood of mice are found to be well within the acceptable laboratory ranges.

TABLE 10

Effects of the Derivatives, QPen_PIBMI, QEst_PIBMI and QAmi_PIBMI on the
Liver and Kidney Functional Parameters and Balance of Electrolytes in the Blood of Mice
48 h Post-treatment

| Treatment | Liver Function | Kidney Function | | Electrolyte Balance | | |
|---|---|---|---|---|---|---|
| | ALP (IU L$^{-1}$) | Creatinine (mg dL$^{-1}$) | Urea Nitrogen (mg dL$^{-1}$) | Sodium ion (mmol L$^{-1}$) | Potassium ion (mmol L$^{-1}$) | Chloride (mmol L$^{-1}$) |
| Without treatment | 150 ± 57 | 0.23 ± 0.07 | 18.4 ± 3.4 | 143 ± 1.6 | 7.2 ± 0.7 | 111.5 ± 1.8 |
| QPen_PIBMI | 179 ± 49 (P > 0.05) | 0.18 ± 0.10 (P > 0.05) | 19 ± 2.3 (P > 0.05) | 144.6 ± 1.6 (P < 0.05) | 6 ± 0.3 (P < 0.05) | 113 ± 1.8 (P > 0.05) |
| QEst_PIBMI | 140 ± 43 (P > 0.05) | 0.25 ± 0.11 (P > 0.05) | 19.1 ± 4.4 (P > 0.05) | 146.1 ± 0.8 (P < 0.05) | 6.0 ± 0.5 (P < 0.05) | 114 ± 2.1 (P < 0.05) |
| QAmi_PIBMI | 157 ± 64 (P > 0.05) | 0.19 ± 0.06 (P > 0.05) | 16.4 ± 2.2 (P > 0.05) | 143 ± 1.7 (P > 0.05) | 7.3 ± 0.5 (P > 0.05) | 109 ± 2.4 (P < 0.05) |
| Laboratory Range* | 209.3 ± 72.4 | 0.38 ± 0.12 | 16 ± 7.2 | 152.3 ± 17 | 8.9 ± 1.5 | 119.3 ± 13.5 |

The polymeric mimics of AMPs do not cause significant acute toxicity to the major organs like liver and kidney and do not interfere with the balance of electrolytes in the blood of mice, 48 h post treatment. Data are expressed as mean±standard deviation, based on the values obtained from 10 mice (n=10) for each independent experiment. Statistical analysis is performed using Student's t-test. Differences are considered statistically significant with probability P<0.05. ALP-Alkaline Phosphatase, IU-International Unit. *Source: Charles River Laboratories.

TABLE 11

Effects of the Derivatives, QPen_PIBMI, QEst_PIBMI and QAmi_PIBMI on the
Liver and Kidney Functional Parameters and Balance of Electrolytes in the Blood of Mice
14 days Post-treatment

| Treatment | Liver Function | Kidney Function | | Electrolyte Balance | | |
|---|---|---|---|---|---|---|
| | ALP (IU L$^{-1}$) | Creatinine (mg dL$^{-1}$) | Urea Nitrogen (mg dL$^{-1}$) | Sodium ion (mmol L$^{-1}$) | Potassium ion (mmol L$^{-1}$) | Chloride (mmol L$^{-1}$) |
| Without treatment | 150 ± 57 | 0.23 ± 0.07 | 18.4 ± 3.4 | 143 ± 1.6 | 7.2 ± 0.7 | 111.5 ± 1.8 |
| QPen_PIBMI | 203 ± 91 (P > 0.05) | 0.18 ± 0.10 (P > 0.05) | 15.1 ± 2.2 (P > 0.05) | 138.1 ± 2.2 (P < 0.05) | 6.4 ± 1 (P < 0.05) | 104.6 ± 3.9 (P > 0.05) |
| QEst_PIBMI | 175 ± 44 (P > 0.05) | 0.13 ± 0.05 (P > 0.05) | 15 ± 2 (P > 0.05) | 139.6 ± 4.2 (P < 0.05) | 6.5 ± 0.5 (P < 0.05) | 106.8 ± 4.7 (P < 0.05) |
| QAmi_PIBMI | 157.3 ± 59.8 (P > 0.05) | 0.14 ± 0.07 (P > 0.05) | 16.7 ± 3.1 (P < 0.05) | 137.5 ± 1.1 (P < 0.05) | 8.2 ± 1 (P < 0.05) | 105.3 ± 2.1 (P < 0.05) |
| Laboratory Range* | 209.3 ± 72.4 | 0.38 ± 0.12 | 16 ± 7.2 | 152.3 ± 17 | 8.9 ± 1.5 | 119.3 ± 13.5 |

Example: 16

In-Vitro Stimulation of Human PBMCs

Fresh human blood is drawn and human peripheral blood mononuclear cells (PBMCs) are isolated using a standard Ficoll-Hypaque density centrifugation technique and the number of PBMCs is determined by trypan blue exclusion. After isolation, human PBMCs are resuspended in RPMI 1640 growth medium (with L-glutamine and sodium bicarbonate, Sigma Aldrich) supplemented with 10% of heat inactivated and low endotoxin fetal bovine serum (FBS, Life Technologies) and 1% penicillin-streptomycin at 37° C. in a humidified-air atmosphere (5% $CO_2$/95% air). The human PBMCs are seeded into 24-well plates (1×10$^6$ cells) in 1 mL of RPMI 1640 complete medium. After 2-3 hr, the cells are stimulated with the polymeric derivatives (30 µg mL$^{-1}$) either in the absence or presence of 100 ng mL$^{-1}$ of E. coli 0111:B4 LPS (Sigma Aldrich). A control experiment is performed using HBSS (Life Techologies) as vehicle control. The cells are incubated for 12-14 hours and then cell culture supernatants are analysed for interleukin-6 (IL-6) using the human ELISA kits (BD Biosciences) following the manufacturer's instructions (FIG. 13 and Table 12).

The stimulation of PBMCs with the polymeric derivatives (30 µg mL$^{-1}$) does not induce any nonspecific immunogenic response clearly observed by no significant secretion of cytokine levels (IL-6) compared to the untreated negative control (HBSS) (Table 12 and FIG. 13). These results suggest that these derivatives do not induce any non-specific immunogenic response and can be used as systemic antimicrobials for various infections. The stimulation of human PMBCs with the polymeric derivatives in the presence of LPS shows that the polymers reduce LPS-induced cytokine levels to background levels (90-95% reduction and in some cases displayed 40-70% reduction) (Table 12 and FIG. 13). These results suggest that the polymeric derivatives proposed in the present invention show anti-inflammatory properties of the host cells and have the potential to activate the immune system for fighting against the microbial infections.

TABLE 12

In-vitro anti-inflammatory properties of the polymeric derivatives against human PBMCs.

| Compound | IL-6 (pg mL$^{-1}$) |
|---|---|
| HBSS | 36 |
| LPS | 1924 |

TABLE 12-continued

In-vitro anti-inflammatory properties of the polymeric derivatives against human PBMCs.

| Compound | IL-6 (pg mL$^{-1}$) |
|---|---|
| QHex_PIBMI | 10 |
| QHex_PIBMI + LPS | 6 |
| QPen_PIBMI | 16 |
| QPen_PIBMI + LPS | 136 |
| QAmi_PIBMI | 13.4 |
| QAmi_PIBMI + LPS | 94 |
| QEst_PIBMI | 13.2 |
| QEst_PIBMI + LPS | 1250 |
| QOEG_PIBMI | 13 |
| QOEG_PIBMI + LPS | 646 |

We claim:

1. A compound of Formula I:

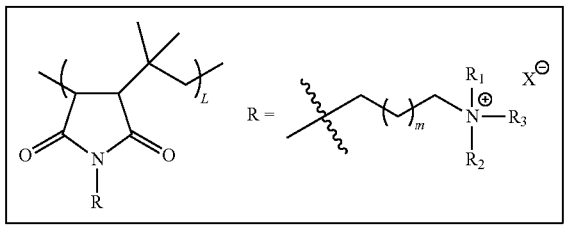

Formula I wherein,

'm' is an integer ranging from 0 to 1,

'L' is an integer ranging from 1 to 100, $R_1$, $R_2$ and $R_3$ are, independently at each occurrence, a hydrogen atom or methyl radical or $C_2$-$C_{40}$ aliphatic radical or $C_3$-$C_{40}$ aromatic radical or any combination thereof, and $X^{\ominus}$ is selected from a group consisting of chloride, bromide and iodide;

and wherein at least one of $R_1$, $R_2$, or $R_3$ comprises a structural moiety selected from a group consisting of:

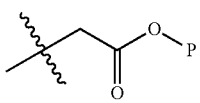

wherein, P is a $C_1$-$C_{24}$ aliphatic saturated radical or a $C_2$-$C_{24}$ aliphatic unsaturated radical,

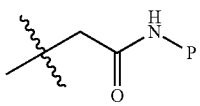

wherein, P is a $C_1$-$C_{24}$ aliphatic saturated radical or a $C_2$-$C_{24}$ aliphatic unsaturated radical,

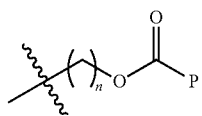

wherein, P is a $C_1$-$C_{24}$ aliphatic saturated radical or a $C_2$-$C_{24}$ aliphatic unsaturated radical, and n is an integer ranging from 1 to 4,

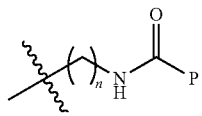

wherein, P is a $C_1$-$C_{24}$ aliphatic saturated radical or a $C_2$-$C_{24}$ aliphatic unsaturated radical, and n is an integer ranging from 1 to 4,

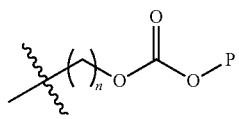

wherein, P is a $C_1$-$C_{24}$ aliphatic saturated radical or a $C_2$-$C_{24}$ aliphatic unsaturated radical, and n is an integer ranging from 1 to 4,

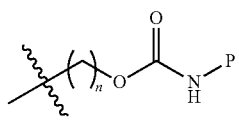

wherein, P is a $C_1$-$C_{24}$ aliphatic saturated radical or a $C_2$-$C_{24}$ aliphatic unsaturated radical, and n is an integer ranging from 1 to 4,

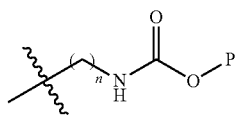

wherein, P is a $C_1$-$C_{24}$ aliphatic saturated radical or a $C_2$-$C_{24}$ aliphatic unsaturated radical, and n is an integer ranging from 1 to 4,

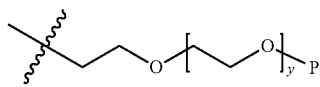

wherein, P is a $C_1$-$C_{24}$ aliphatic saturated radical or a $C_2$-$C_{24}$ aliphatic unsaturated radical, and y is an integer ranging from 0 to 3,

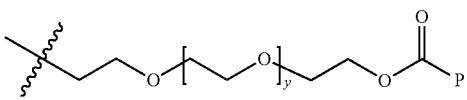

wherein, P is a $C_1$-$C_{24}$ aliphatic saturated radical or a $C_2$-$C_{24}$ aliphatic unsaturated radical, and y is an integer ranging from 0 to 3, and

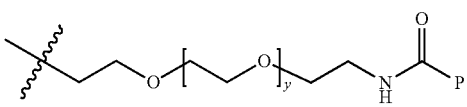

wherein, P is a $C_1$-$C_{24}$ aliphatic saturated radical or a $C_2$-$C_{24}$ aliphatic unsaturated radical, and y is an integer ranging from 0 to 3.

2. The compound of claim 1 for use in the treatment of a bacterial infection.

3. The compound of claim 2, wherein the bacterial infection caused by a Gram-positive bacterium or a Gram-negative bacterium.

4. The compound of claim 1 for use in the treatment of a bacterial infection wherein the bacterial infection caused by a drug-resistant bacterium.

5. The compound of claim 1 for use in the treatment of sepsis.

6. A composition comprising the compound of Formula I

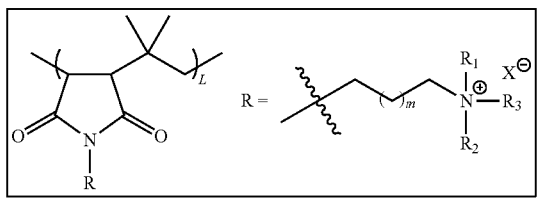

wherein,
- 'm' is an integer ranging from 0 to 1,
- 'L' is an integer ranging from 1 to 100,
- $R_1$, $R_2$ and $R_3$ are, independently at each occurrence, a hydrogen atom or methyl radical or
- $C_2$-$C_{40}$ aliphatic radical or $C_3$-$C_{40}$ aromatic radical or any combination thereof, and
- $X^\ominus$ is selected from a group consisting of chloride, bromide and iodide;

and wherein at least one of $R_1$, $R_2$, or $R_3$ comprises a structural moiety selected from a group consisting of:

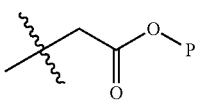

wherein, P is a $C_1$-$C_{24}$ aliphatic saturated radical or a $C_2$-$C_{24}$ aliphatic unsaturated radical,

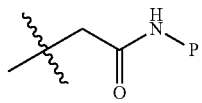

wherein, P is a $C_1$-$C_{24}$ aliphatic saturated radical or a $C_2$-$C_{24}$ aliphatic unsaturated radical,

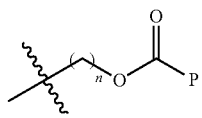

wherein, P is a $C_1$-$C_{24}$ aliphatic saturated radical or a $C_2$-$C_{24}$ aliphatic unsaturated radical, and n is an integer ranging from 1 to 4,

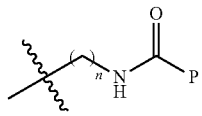

wherein, P is a $C_1$-$C_{24}$ aliphatic saturated radical or a $C_2$-$C_{24}$ aliphatic unsaturated radical, and n is an integer ranging from 1 to 4,

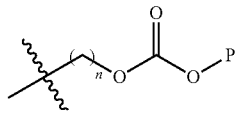

wherein, P is a $C_1$-$C_{24}$ aliphatic saturated radical or a $C_2$-$C_{24}$ aliphatic unsaturated radical, and n is an integer ranging from 1 to 4,

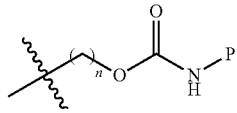

wherein, P is a $C_1$-$C_{24}$ aliphatic saturated radical or a $C_2$-$C_{24}$ aliphatic unsaturated radical, and n is an integer ranging from 1 to 4,

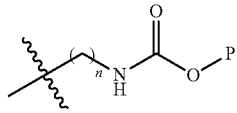

wherein, P is a $C_1$-$C_{24}$ aliphatic saturated radical or a $C_2$-$C_{24}$ aliphatic unsaturated radical, and n is an integer ranging from 1 to 4,

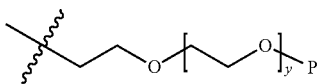

wherein, P is a $C_1$-$C_{24}$ aliphatic saturated radical or a $C_2$-$C_{24}$ aliphatic unsaturated radical, and y is an integer ranging from 0 to 3,

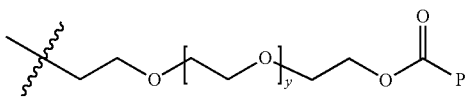

wherein, P is a $C_1$-$C_{24}$ aliphatic saturated radical or a $C_2$-$C_{24}$ aliphatic unsaturated radical, and y is an integer ranging from 0 to 3,
and

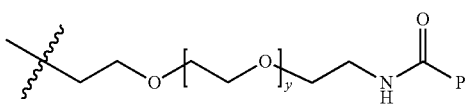

wherein, P is a $C_1$-$C_{24}$ aliphatic saturated radical or a $C_2$-$C_{24}$ aliphatic unsaturated radical, and y is an integer ranging from 0 to 3.

7. A method of treatment of a bacterial infection in a subject comprising: administering to the subject an effective amount of the composition of claim 6.

8. The method of claim 7 wherein the bacterial infection is caused by a Gram-positive bacterium or a Gram-negative bacterium.

9. The method of claim 7, wherein the bacterial infection is caused by a drug-resistant bacterium.

10. The method of claim 7, wherein the bacterial infection is caused by *Escherichia coli, Staphylococcus aureus, Pseudomonas aeruginosa, Klebsiella pneumoniae, Enterococcus faecium*, methicillin resistant *Staphylococcus aureus* and vancomycin resistant *Enterococcus faecium* or a combination thereof.

11. A method of suppressing inflammation comprising administering to a subject suffering from sepsis the composition of claim 6.

12. An article comprising the composition of claim 6.

13. The composition of claim 6, wherein the composition is a nanoparticle composition.

14. A method of preparing the nanoparticle composition of claim 13, said method comprising dispersing the compound of Formula I in a solvent system comprising a hydrophilic solvent, a hydrophobic solvent, or a mixture of both.

15. A method of treatment of a bacterial infection in a subject comprising: administering to the subject an effective amount of the nanoparticle composition of claim 13.

16. The method of claim 15 wherein the bacterial infection is caused by a Gram-positive bacterium or a Gram-negative bacterium.

17. The method of claim 15, wherein the bacterial infection is caused by a drug-resistant bacterium.

18. The method of claim 15, wherein the bacterial infection is caused by *Escherichia coli, Staphylococcus aureus, Pseudomonas aeruginosa, Klebsiella pneumoniae, Enterococcus faecium*, methicillin resistant *Staphylococcus aureus* and vancomycin resistant *Enterococcus faecium* or a combination thereof.

19. A method of suppressing inflammation comprising administering to a subject suffering from sepsis the nanoparticle composition of claim 13.

20. An article comprising the nanoparticle composition of claim 13.

* * * * *